United States Patent
Lang et al.

(10) Patent No.: US 10,206,967 B2
(45) Date of Patent: Feb. 19, 2019

(54) COMPOSITIONS AND METHODS FOR TREATING HEART DISEASE AND/OR INJURY

(71) Applicants: CASE WESTERN RESERVE UNIVERSITY, Cleveland, OH (US); OREGON HEALTH & SCIENCE UNIVERSITY, Portland, OR (US)

(72) Inventors: Bradley T. Lang, Cleveland, OH (US); Jerry Silver, Cleveland, OH (US); Ryan Gardner, Portland, OR (US); Beth Habecker, Portland, OR (US)

(73) Assignees: CASE WESTERN RESERVE UNIVERSITY, Cleveland, OH (US); OREGON HEALTH & SCIENCE UNIVERSITY, Portland, OR (US)

( * ) Notice: Subject to any disclaimer, the term of this patent is extended or adjusted under 35 U.S.C. 154(b) by 0 days.

(21) Appl. No.: 15/257,636

(22) Filed: Sep. 6, 2016

(65) Prior Publication Data

US 2017/0035830 A1 Feb. 9, 2017

Related U.S. Application Data

(63) Continuation-in-part of application No. PCT/US2015/018971, filed on Mar. 5, 2015, which is a continuation-in-part of application No. 14/391,589, filed as application No. PCT/US2013/035831 on Apr. 9, 2013, now Pat. No. 9,937,242.

(60) Provisional application No. 61/948,396, filed on Mar. 5, 2014, provisional application No. 61/621,623, filed on Apr. 9, 2012.

(51) Int. Cl.
 C07K 7/08 (2006.01)
 A61K 38/00 (2006.01)
 C07K 14/00 (2006.01)

(52) U.S. Cl.
 CPC .............. *A61K 38/005* (2013.01); *C07K 7/08* (2013.01); *C07K 14/00* (2013.01); *C07K 2319/10* (2013.01)

(58) Field of Classification Search
 None
 See application file for complete search history.

(56) References Cited

U.S. PATENT DOCUMENTS

| | | |
|---|---|---|
| 2004/0138255 A1 | 7/2004 | Huang et al. |
| 2009/0042872 A1 | 2/2009 | Ryu et al. |
| 2009/0202544 A1 | 8/2009 | Suciu-Foca |
| 2012/0045459 A1 | 2/2012 | Mackeigan et al. |
| 2012/0231014 A1 | 9/2012 | Flanagan |
| 2014/0045762 A1 | 2/2014 | Flanagan |

FOREIGN PATENT DOCUMENTS

| | | |
|---|---|---|
| WO | 02083182 A2 | 10/2002 |
| WO | 2009072726 A1 | 6/2009 |
| WO | WO 2010/129681 A1 * | 11/2010 |
| WO | 2012019086 A2 | 9/2012 |
| WO | 2013155103 A1 | 10/2013 |

OTHER PUBLICATIONS

Zipes "Influence of Myocardial Ischemia and Infarction on Autonomic Innervation of Heart," Circulation. 1990;82:1095-1105 (Year: 1990).*
Extended Search Report dated Oct. 30, 2015.
Koren, et al., "Inhibition of the protein tyrosine phosphatase PTP1B: Potential therapy for obesity, insulin resistance and type-2 diabetes mellitus", Best Practice and Research Clinical Endocrinology and Metabolism, vol. 21, No. 4, pp. 321-640, Dec. 31, 2007.
Aricescu, A. Radu, et al., "Heparan Sulfate Proteoglycans Are Ligands for Receptor Protein Tyrosine Phosphatase σ", Molecular and Cellular Biology, Mar. 2002, p. 1881-1892, vol. 22, No. 6.
Brown, Joshua M., et al., "A sulfated carbohydrate epitope inhibits axon regeneration after injury", PNAS, Mar. 27, 2012, vol. 109, No. 13, pp. 4768-4773.
Carey, D.J., et al. "Association of Cell Surface Heparan Sulfate Proteoglycans of Schwann Cells with Extracellular Matrix Proteins", J. Biol. Chem. 1990, 265:20627-20633.
Coles, Charlotte, et al. Proteoglycan-Specific Molecular Switch for RPTPσ Clustering and Neuronal Extension, Science. Apr. 22, 2011, 332(6028): 484-488.
Cortes, Mauricio, et al., "Sulfation if Chondroitin Sulfate Proteoglycans is necessary for proper Indian hedgehog signaling in the developing growth plate", Development 136, 1697-1706 (2009).
Dickendesher, Travis, L., "NgR1 and NgR3 are Receptors for Chondroitin Sulfate Proteoglycans", Nat. Neurosci.; 15(5): 703-712.
Fisher, Daniel, et al., "LAR is a functional receptor for CSPG Axon Growth Inhibitors", J. Neurosci. Oct. 5, 2011; 31(40):14051-14066.
Horn, Kevin, et al., "Another barrier to regeneration in the CNS: Activated macrophages induce extensive retraction of dystrophic axons through direct physical interactions", J. Neurosci. Sep. 17, 2008; 28(38):9330-9341.
Majeti, Ravindra, et al., "Dimerization-Induced Inhibition of Receptor Protein Tyrosine Phosphatase Function Through an Inhibitory Wedge", Science vol. 279, Jan. 2, 1998.
Shen, Yingjie, et al., "PTPσ is a Receptor for Chondroitin Sulfate Proteoglycan, an Inhibitor of Neural Regeneration", Science. Oct. 23, 2009; 326(5952: 592-596.
Tom, Veronica J., et al., "Studies in the Development and Behaviro of the Dystrophic Growth Cone, the Hallmark of Regeneration Failure, and an In Vitro Model of the Glial Scar and after Spinal Injury", The journal of Neuroscience, Jul. 21, 2004, 24(29):6531-6539.
Xie, Youmei, et al., "Protein-Tyrosine Phosphatase (PTP) Wedge Domain Peptides: A Novel Approach for Inhibition of PTP Function and Augmentation of Protein-Tyrosine Kinase Function", J. Biol. Chem. 2006, 281-16482-16492.

* cited by examiner

*Primary Examiner* — Christina Bradley
(74) *Attorney, Agent, or Firm* — Tarolli, Sundheim, Covell & Tummino, LLP

(57) ABSTRACT

A method of treating heart disease and/or injury in a subject includes administering to the subject a therapeutic agent that inhibits one or more of catalytic activity, signaling, and function of PTPσ.

16 Claims, 2 Drawing Sheets

Specification includes a Sequence Listing.

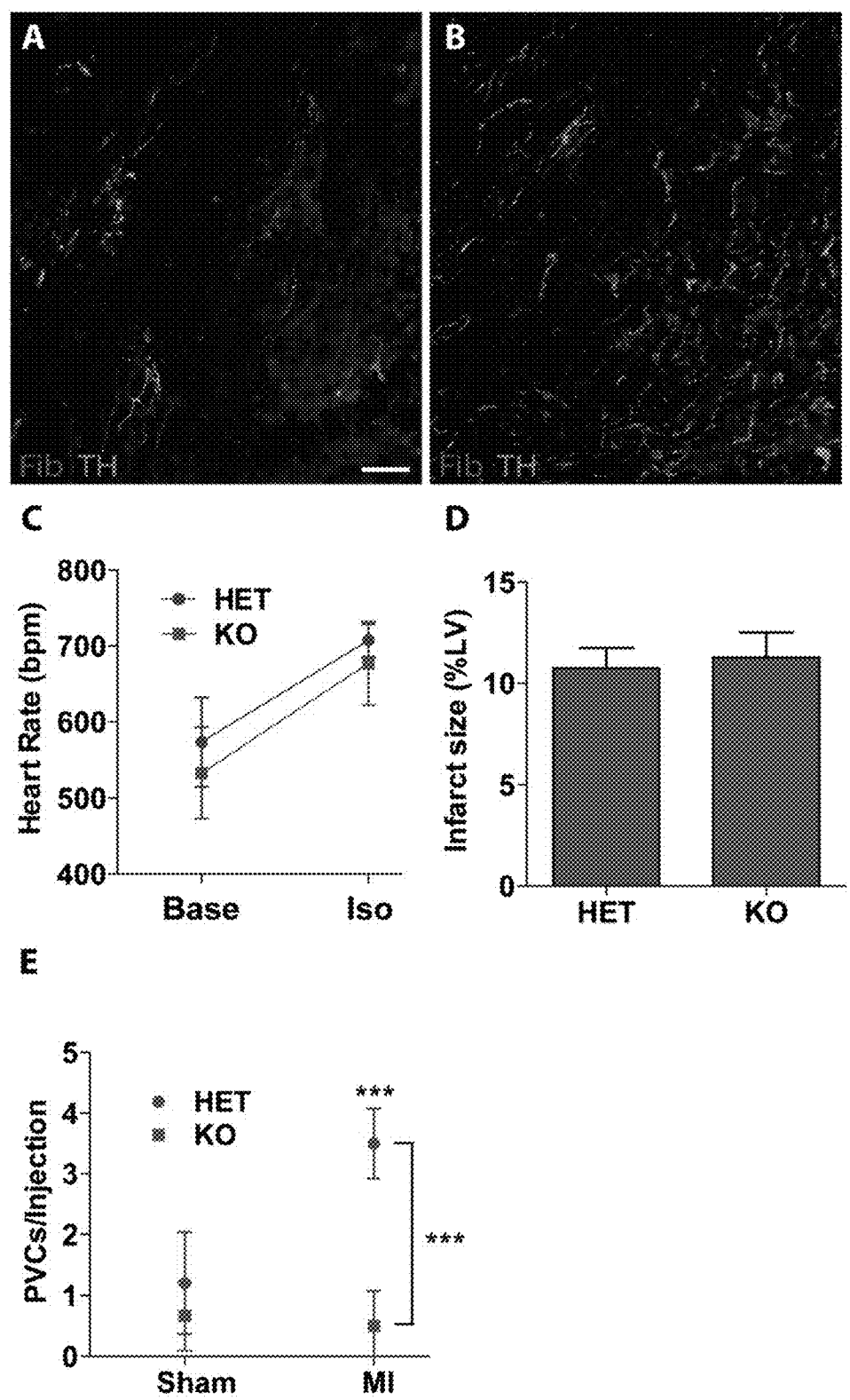
Figs. 1A-E

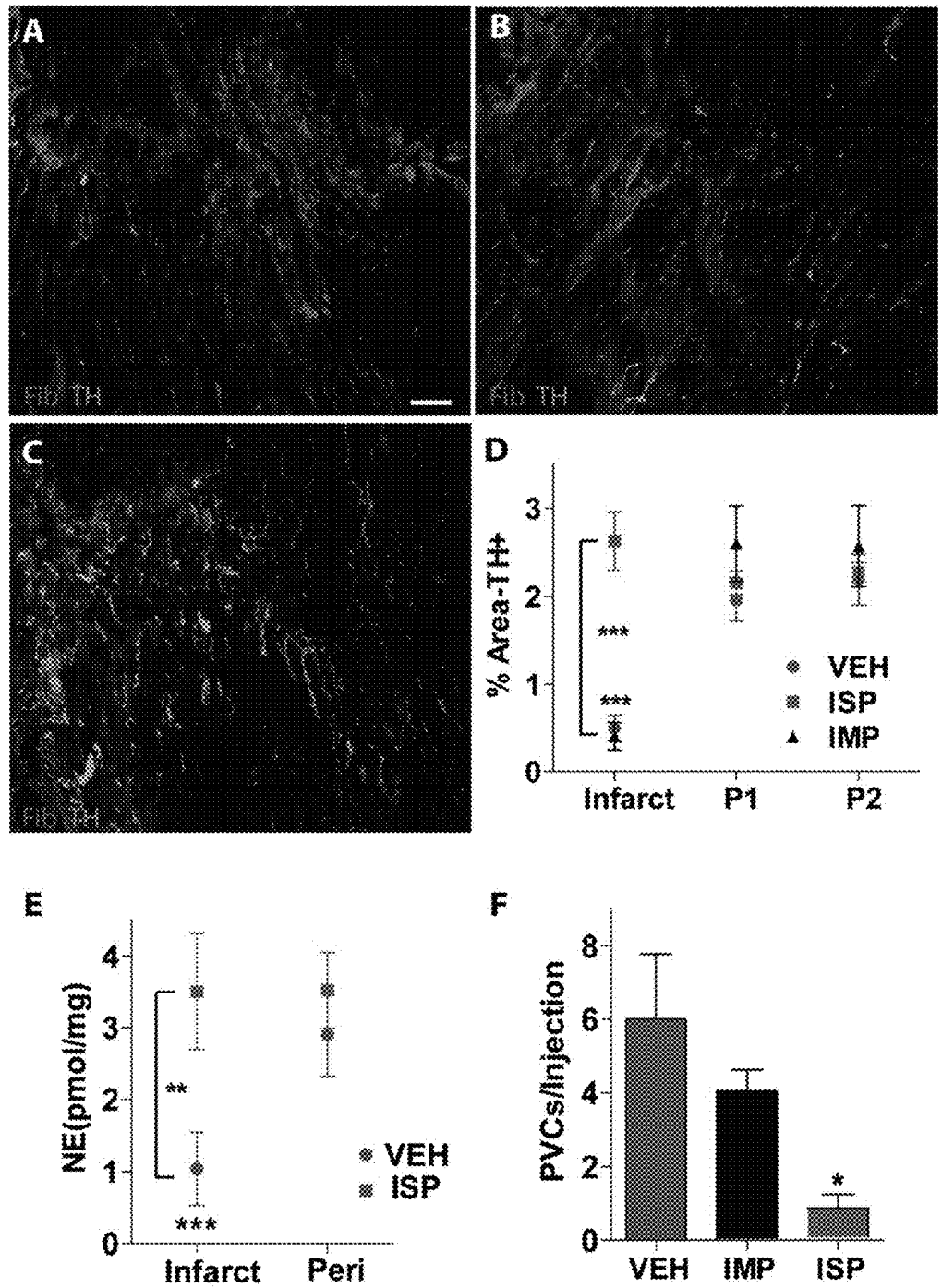
Figs. 2A-F

COMPOSITIONS AND METHODS FOR TREATING HEART DISEASE AND/OR INJURY

RELATED APPLICATION

This application is a Continuation-in-Part of PCT/US2015/018971, filed Mar. 5, 2015, which claims priority to U.S. Provisional Application No. 61/948,396, filed Mar. 5, 2014, this application is also a Continuation-in-Part of U.S. patent application Ser. No. 14/391,589, which is a National Phase Filing of PCT/US2013/035831, filed Apr. 9, 2013, which claims priority to U.S. Provisional Patent Application Ser. No. 61/621,623, filed Apr. 9, 2012, the subject matter of which are incorporated herein by reference in their entirety.

GOVERNMENT FUNDING

This invention was made with government support under Grant No. NS25713 awarded by National Institute of Neurological Disorders and Stroke. The United States government has certain rights to the invention.

TECHNICAL FIELD

This application relates to compositions and methods for treating heart disease and/or injury as well as to compositions and methods of promoting and/or restoring innervation of myocardial tissue of a subject in need thereof.

BACKGROUND

Survivors of myocardial infarction (MI) remain at high risk for cardiac arrhythmias and sudden cardiac death. The infarct, or scar, generates an anatomical substrate for the initiation of re-entrant arrhythmias and numerous studies indicate that altered sympathetic neurotransmission in the region of the scar plays a key role in the onset of these untoward post-infarct events. The transmural (epicardial to endocardial) gradient in action potential duration (APD), which is accompanied by a transmural gradient in sympathetic innervation density, is critical for normal activation and repolarization of the left ventricle. Norepinephrine (NE) released from sympathetic nerves activates cardiac β-adrenergic receptors (β-AR) to modulate the rate of myocyte repolarization by altering $Ca^{2+}$ homeostasis, and simply disrupting the transmural gradient of sympathetic innervation in an otherwise normal heart is arrhythmogenic.

Cardiac sympathetic function is altered in a region-specific manner following MI, and studies in animals and humans reveal denervation of the infarct and adjacent viable (peri-infarct) myocardium. Three recent studies in patients with implanted cardioverter defibrillators (ICDs) suggest that the amount of sympathetic denervation after MI predicts the probability of serious ventricular arrhythmias. Furthermore, a detailed electrical mapping study in intact human hearts revealed that sympathetic denervation of the normal myocardium adjacent to the scar resulted in β-AR agonist supersensitivity and increased dispersion of repolarization that as arrhythmogenic.

SUMMARY

Embodiments described herein relate to compositions and methods for treating heart disease and/or injury as well as to compositions and methods of promoting and/or restoring innervation or sympathetic function of myocardial tissue of a subject in need thereof. In some embodiments, the methods can include administering to a subject or myocardial tissue of a subject a therapeutically effective amount of a therapeutic agent that inhibits one or more of catalytic activity, signaling, and function of PTPσ of neurons or nerve cells, such as cardiac sympathetic nerves, that extend to or within the myocardial tissue. In some embodiments, the heart disease or injury comprises at least one of myocardial infarction, myocardial ischemia/reperfusion injury, cardiac denervation hypersensitivity, arrhythmia, chronic ischemia, and myocardial surgery and/or transplantation. In other embodiments, the therapeutic agent can be administered to the myocardial tissue to promote and/or restore functional sympathetic innervation of the myocardial tissue, reduce arrhythmic susceptibility, normalize electrophysiology of the myocardial tissue, and/or mitigate heterogeneity of sympathetic transmission of the myocardial tissue.

In some embodiments, the therapeutic agent includes a therapeutic peptide having an amino acid sequence with a sequence identity that is at least about 65%, at least about 70%, at least about 75%, at least about 80%, at least about 85%, at least about 90%, or at least about 95% homologous or identical to about 10 to about 20 consecutive amino acids of the wedge domain of PTPσ. For example, therapeutic agent can include a therapeutic peptide selected from the group consisting of SEQ ID NOs: 1-25 and 32.

In still other embodiments, the therapeutic agent can include a therapeutic peptide that has a sequence identity at least about 65%, at least about 70%, at least about 75%, at least about 80%, at least about 85%, at least about 90%, or at least about 95% homologous to the amino acid sequence of SEQ ID NO: 32. The therapeutic peptide can include, for example, a conservative substitution of an amino acid of at least one, two, three, or four of residue 4, 5, 6, 7, 9, 10, 12, or 13 of SEQ ID NO: 32.

In other embodiments, the therapeutic agent includes a transport moiety that is linked to the therapeutic peptide and facilitates uptake of the therapeutic peptides by a nerve cell, such as a cardiac sympathetic nerve. For example, the transport moiety can be an HIV Tat transport moiety.

In still other embodiments, the therapeutic agent is administered locally to myocardial tissue of the subject or systemically to the subject to treat myocardial tissue.

In some embodiments the heart injury is a myocardial infarction and the therapeutic agent is administered to the infarct or peri-infarct region of the heart.

In yet other embodiments, the therapeutic peptide is expressed in a cardiac nerve cell.

BRIEF DESCRIPTION OF THE DRAWINGS

FIGS. 1(A-E) illustrate: (A-B) images showing heart sections from ptprs+/−(A) and ptprs−/− (B) mice stained for TH to and fibrinogen; (C) a plot showing heart rate in both genotypes before (Base) and after (ISO) 10 μg isoproterenol injection (mean±SEM, n=8/genotype); (D) a graph comparing infarct size in HET and KO hearts following 35 min of occlusion (mean±SEM, n=4/group); and (E) a plot showing isoproterenol induced PVCs in conscious Sham HET and KO mice.

FIGS. 2(A-F) illustrate: (A-C) images of infarcted LV from mice treated with vehicle (A), IMP (B), or ISP (C); (D) a plot showing quantification of TH+ fiber density within the infarct, the area immediately adjacent to the infarct (P1), and distal peri-infarct myocardium (P2; 540 m from infarct) 14 day post-MI (mean±SEM, n=5/group; *p<0.001); (E) a plot showing norepinephrine (NE) content in the infarct and peri-infarct LV (P1 and P2 combined) (mean±SEM; n=5; p<0.01, ***p<0.001); and (F) a graph showing isoproterenol induced PVCs in conscious mice 14 days after MI (mean±SEM, n=5-6; *p<0.05 vs vehicle and IMP).

DETAILED DESCRIPTION

The embodiments described herein are not limited to the particular methodology, protocols, and reagents, etc., and as such may vary. The terminology used herein is for the purpose of describing particular embodiments only, and is not intended to limit the scope of the present invention, which is defined solely by the claims. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and does not constitute any admission as to the correctness of the dates or contents of these documents.

Unless otherwise defined, scientific and technical terms used herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art.

As used herein, "one or more of a, b, and c" means a, b, c, ab, ac, bc, or abc. The use of "or" herein is the inclusive or.

The term "administering" to a patient includes dispensing, delivering or applying an active compound in a pharmaceutical formulation to a subject by any suitable route for delivery of the active compound to the desired location in the subject (e.g., to thereby contact a desired cell such as a desired neuron), including administration into the cerebrospinal fluid or across the blood-brain barrier, delivery by either the parenteral or oral route, intramuscular injection, subcutaneous or intradermal injection, intravenous injection, buccal administration, transdermal delivery and administration by the rectal, colonic, vaginal, intranasal or respiratory tract route. The agents may, for example, be administered to a comatose, anesthetized or paralyzed subject via an intravenous injection or may be administered intravenously to a pregnant subject to stimulate axonal growth in a fetus. Specific routes of administration may include topical application (such as by eyedrops, creams or erodible formulations to be placed under the eyelid, intraocular injection into the aqueous or the vitreous humor, injection into the external layers of the eye, such as via subconjunctival injection or subtenon injection, parenteral administration or via oral routes.

The term "antibody", includes human and animal mAbs, and preparations of polyclonal antibodies, synthetic antibodies, including recombinant antibodies (antisera), chimeric antibodies, including humanized antibodies, anti-idiotopic antibodies and derivatives thereof. A portion or fragment of an antibody refers to a region of an antibody that retains at least part of its ability (binding specificity and affinity) to bind to a specified epitope. The term "epitope" or "antigenic determinant" refers to a site on an antigen to which antibody paratope binds. Epitopes formed from contiguous amino acids are typically retained on exposure to denaturing solvents whereas epitopes formed by tertiary folding are typically lost on treatment with denaturing solvents. An epitope typically includes at least 3, at least 5, or 8 to 10, or about 13 to 15 amino acids in a unique spatial conformation. Methods of determining spatial conformation of epitopes include, for example, x-ray crystallography and 2-dimensional nuclear magnetic resonance.

The terms axonal "growth" or "outgrowth" (also referred to herein as "neuronal outgrowth") includes the process by which axons or dendrites extend from a neuron. The outgrowth can result in a new neuritic projection or in the extension of a previously existing cellular process. "Stimulating axonal growth" means promoting axonal outgrowth.

The terms "cardiac tissue", "heart", "heart tissue", or "myocardial tissue" includes the myocardium, epicardium, endocardium, and pericardium (the pericardial sac) of the heart. The term as used herein also refers to the great vessels leading to or from the heart. The term as used herein also refers to portions of the vagus nerve and sympathetic nerves that innervate the heart.

The term "dieback" refers to axonal retraction that occurs as a result of trauma to the axon.

The terms "chimeric protein" or "fusion protein" refer to a fusion of a first amino acid sequence encoding a polypeptide with a second amino acid sequence defining a domain (e.g., polypeptide portion) foreign to and not substantially homologous with the domain of the first polypeptide. A chimeric protein may present a foreign domain, which is found (albeit in a different protein) in an organism, which also expresses the first protein, or it may be an "interspecies", "intergenic", etc. fusion of protein structures expressed by different kinds of organisms.

The term "contacting neurons" or "treating neurons" refers to any mode of agent delivery or "administration," either to cells or to whole organisms, in which the agent is capable of exhibiting its pharmacological effect in neurons. "Contacting neurons" includes both in vivo and in vitro methods of bringing an agent of the invention into proximity with a neuron. Suitable modes of administration can be determined by those skilled in the art and such modes of administration may vary between agents. For example, when axonal growth of neurons is stimulated ex vivo, agents can be administered, for example, by transfection, lipofection, electroporation, viral vector infection, or by addition to growth medium.

An "effective amount" of an agent or therapeutic peptide is an amount sufficient to achieve a desired therapeutic or pharmacological effect, such as an amount that is capable of activating the growth of neurons. An effective amount of an agent as defined herein may vary according to factors such as the disease state, age, and weight of the subject, and the ability of the agent to elicit a desired response in the subject. Dosage regimens may be adjusted to provide the optimum therapeutic response. An effective amount is also one in which any toxic or detrimental effects of the active compound are outweighed by the therapeutically beneficial effects.

The term "expression" refers to the process by which nucleic acid is translated into peptides or is transcribed into RNA, which, for example, can be translated into peptides, polypeptides or proteins. If the nucleic acid is derived from genomic DNA, expression may, if an appropriate eukaryotic host cell or organism is selected, include splicing of the mRNA. For heterologous nucleic acid to be expressed in a host cell, it must initially be delivered into the cell and then, once in the cell, ultimately reside in the nucleus.

The term "genetic therapy" involves the transfer of heterologous DNA to cells of a mammal, particularly a human, with a disorder or conditions for which therapy or diagnosis is sought. The DNA is introduced into the selected target cells in a manner such that the heterologous DNA is expressed and a therapeutic product encoded thereby is produced. Alternatively, the heterologous DNA may in some manner mediate expression of DNA that encodes the therapeutic product; it may encode a product, such as a peptide or RNA that in some manner mediates, directly or indirectly, expression of a therapeutic product. Genetic therapy may also be used to deliver nucleic acid encoding a gene product to replace a defective gene or supplement a gene product produced by the mammal or the cell in which it is introduced. The introduced nucleic acid may encode a therapeutic compound, such as a growth factor inhibitor thereof, or a tumor necrosis factor or inhibitor thereof, such as a receptor therefore, that is not normally produced in the mammalian host or that is not produced in therapeutically effective amounts or at a therapeutically useful time. The heterologous DNA encoding the therapeutic product may be modified prior to introduction into the cells of the afflicted host in order to enhance or otherwise alter the product or expression thereof.

The term "gene" or "recombinant gene" refers to a nucleic acid comprising an open reading frame encoding a polypeptide, including both exon and (optionally) intron sequences.

The term "heterologous nucleic acid sequence" is typically DNA that encodes RNA and proteins that are not normally produced in vivo by the cell in which it is expressed or that mediates or encodes mediators that alter expression of endogenous DNA by affecting transcription, translation, or other regulatable biochemical processes. A heterologous nucleic acid sequence may also be referred to as foreign DNA. Any DNA that one of skill in the art would recognize or consider as heterologous or foreign to the cell in which it is expressed is herein encompassed by heterologous DNA. Examples of heterologous DNA include, but are not limited to, DNA that encodes traceable marker proteins, such as a protein that confers drug resistance, DNA that encodes therapeutically effective substances, such as anticancer agents, enzymes and hormones, and DNA that encodes other types of proteins, such as antibodies. Antibodies that are encoded by heterologous DNA may be secreted or expressed on the surface of the cell in which the heterologous DNA has been introduced.

The terms "homology" and "identity" are used synonymously throughout and refer to sequence similarity between two peptides or between two nucleic acid molecules. Homology can be determined by comparing a position in each sequence, which may be aligned for purposes of comparison. When a position in the compared sequence is occupied by the same base or amino acid, then the molecules are homologous or identical at that position. A degree of homology or identity between sequences is a function of the number of matching or homologous positions shared by the sequences.

The term "neuronal migration" refers to the ability of neuronal cells to migrate or neuronal processes to migrate such as an axonal or dendritic migration.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into a target tissue (e.g., the cardiac tissue), such that it enters the animal's system and, thus, is subject to metabolism and other like processes, for example, subcutaneous administration.

The term "patient" or "subject" or "animal" or "host" refers to any mammal. The subject may be a human, but can also be a mammal in need of veterinary treatment, e.g., domestic animals (e.g., dogs, cats, and the like), farm animals (e.g., cows, sheep, fowl, pigs, horses, and the like) and laboratory animals (e.g., rats, mice, guinea pigs, and the like).

The term "peripheral nervous system (PNS) neurons" includes the neurons which reside or extend outside of the CNS. PNS is intended to include the neurons commonly understood as categorized in the peripheral nervous system, including sensory neurons and motor neurons.

The terms "polynucleotide sequence" and "nucleotide sequence" are also used interchangeably herein.

The terms "peptide" or "polypeptide" are used interchangeably herein and refer to compounds consisting of from about 2 to about 90 amino acid residues, inclusive, wherein the amino group of one amino acid is linked to the carboxyl group of another amino acid by a peptide bond. A peptide can be, for example, derived or removed from a native protein by enzymatic or chemical cleavage, or can be prepared using conventional peptide synthesis techniques (e.g., solid phase synthesis) or molecular biology techniques (see Sambrook et al., MOLECULAR CLONING: LAB. MANUAL (Cold Spring Harbor Press, Cold Spring Harbor, N.Y., 1989)). A "peptide" can comprise any suitable L- and/or D-amino acid, for example, common a-amino acids (e.g., alanine, glycine, valine), non-a-amino acids (e.g., P-alanine, 4-aminobutyric acid, 6aminocaproic acid, sarcosine, statine), and unusual amino acids (e.g., citrulline, homocitruline, homoserine, norleucine, norvaline, ornithine). The amino, carboxyl and/or other functional groups on a peptide can be free (e.g., unmodified) or protected with a suitable protecting group. Suitable protecting groups for amino and carboxyl groups, and means for adding or removing protecting groups are known in the art. See, e.g., Green & Wuts, PROTECTING GROUPS IN ORGANIC SYNTHESIS (John Wiley & Sons, 1991). The functional groups of a peptide can also be derivatized (e.g., alkylated) using art-known methods.

Peptides can be synthesized and assembled into libraries comprising a few too many discrete molecular species. Such libraries can be prepared using well-known methods of combinatorial chemistry, and can be screened as described herein or using other suitable methods to determine if the library comprises peptides which can antagonize CSPG-PTPσ interaction. Such peptide antagonists can then be isolated by suitable means.

The term "peptidomimetic", refers to a protein-like molecule designed to mimic a peptide. Peptidomimetics typically arise either from modification of an existing peptide, or by designing similar systems that mimic peptides, such as peptoids and β-peptides. Irrespective of the approach, the altered chemical structure is designed to advantageously adjust the molecular properties such as, stability or biological activity. These modifications involve changes to the peptide that do not occur naturally (such as altered backbones and the incorporation of nonnatural amino acids).

The terms "prevent" or "preventing" refer to reducing the frequency or severity of a disease or condition. The term does not require an absolute preclusion of the disease or condition. Rather, this term includes decreasing the chance for disease occurrence. For example, disclosed are methods of reducing the occurrence and/or severity of a cardiac arrhythmia in a subject, comprising administering to cardiac tissue of the subject a therapeutically effective amount of a composition comprising a therapeutic agent.

The term "retraction" refers to the receding of the axon away from the site of injury, such as from where the glial scar forms. Here, the end of regenerating axons stop extending and become dystrophic. These dystrophic ends then can recede further from the glial scar and the site of injury.

A polynucleotide sequence (DNA, RNA) is "operatively linked" to an expression control sequence when the expression control sequence controls and regulates the transcription and translation of that polynucleotide sequence. The term "operatively linked" includes having an appropriate start signal (e.g., ATG) in front of the polynucleotide sequence to be expressed, and maintaining the correct reading frame to permit expression of the polynucleotide sequence under the control of the expression control sequence, and production of the desired polypeptide encoded by the polynucleotide sequence.

The term "recombinant," as used herein, means that a protein is derived from a prokaryotic or eukaryotic expression system.

The term "therapeutically effective" means that the amount of the composition used is of sufficient quantity to ameliorate one or more causes, symptoms, or sequelae of a disease or disorder. Such amelioration only requires a reduction or alteration, not necessarily elimination, of the causes, symptoms, or sequelae of a disease or disorder.

The term "tissue-specific promoter" means a nucleic acid sequence that serves as a promoter, i.e., regulates expression of a selected nucleic acid sequence operably linked to the promoter, and which affects expression of the selected nucleic acid sequence in specific cells of a tissue, such as cells of epithelial cells. The term also covers so-called "leaky" promoters, which regulate expression of a selected nucleic acid primarily in one tissue, but cause expression in other tissues as well. The term "transfection" is used to refer to the uptake of foreign DNA by a cell. A cell has been "transfected" when exogenous DNA has been introduced inside the cell membrane. A number of transfection techniques are generally known in the art. See, e.g., Graham et al., Virology 52:456 (1973); Sambrook et al., Molecular Cloning: A Laboratory Manual (1989); Davis et al., Basic Methods in Molecular Biology (1986); Chu et al., Gene 13:197 (1981). Such techniques can be used to introduce one or more exogenous DNA moieties, such as a nucleotide integration vector and other nucleic acid molecules, into suitable host cells. The term captures chemical, electrical, and viral-mediated transfection procedures.

The terms "transcriptional regulatory sequence" is a generic term used throughout the specification to refer to nucleic acid sequences, such as initiation signals, enhancers, and promoters, which induce or control transcription of protein coding sequences with which they are operably linked. In some examples, transcription of a recombinant gene is under the control of a promoter sequence (or other transcriptional regulatory sequence), which controls the expression of the recombinant gene in a cell-type in which expression is intended. It will also be understood that the recombinant gene can be under the control of transcriptional regulatory sequences which are the same or which are different from those sequences, which control transcription of the naturally occurring form of a protein.

The term "sympathetic nervous system" refers to the thoracolumbar division of the autonomic nervous system, which is responsible for helping to regulate a variety of body functions, including heart rate, breathing, sweating, and digestion.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "vector" refers to a nucleic acid molecule capable of transporting another nucleic acid to which it has been linked. Preferred vectors are those capable of one or more of, autonomous replication and expression of nucleic acids to which they are linked. Vectors capable of directing the expression of genes to which they are operatively linked are referred to herein as "expression vectors".

The term "wild type" refers to the naturally-occurring polynucleotide sequence encoding a protein, or a portion thereof, or protein sequence, or portion thereof, respectively, as it normally exists in vivo. As used herein, the term "nucleic acid" refers to polynucleotides, such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

The agents, compounds, compositions, antibodies, etc. used in the methods described herein are considered to be purified and/or isolated prior to their use. Purified materials are typically "substantially pure", meaning that a nucleic acid, polypeptide or fragment thereof, or other molecule has been separated from the components that naturally accompany it. Typically, the polypeptide is substantially pure when it is at least 60%, 70%, 80%, 90%, 95%, or even 99%, by weight, free from the proteins and other organic molecules with which it is associated naturally. For example, a substantially pure polypeptide may be obtained by extraction from a natural source, by expression of a recombinant nucleic acid in a cell that does not normally express that protein, or by chemical synthesis. "Isolated materials" have been removed from their natural location and environment. In the case of an isolated or purified domain or protein fragment, the domain or fragment is substantially free from amino acid sequences that flank the protein in the naturally-occurring sequence. The term "isolated DNA" means DNA has been substantially freed of the genes that flank the given DNA in the naturally occurring genome. Thus, the term "isolated DNA" encompasses, for example, cDNA, cloned genomic DNA, and synthetic DNA.

The terms "portion", "fragment", "variant", "derivative" and "analog", when referring to a polypeptide include any polypeptide that retains at least some biological activity referred to herein (e.g., inhibition of an interaction such as binding). Polypeptides as described herein may include portion, fragment, variant, or derivative molecules without limitation, as long as the polypeptide still serves its function. Polypeptides or portions thereof of the present invention may include proteolytic fragments, deletion fragments and in particular, or fragments that more easily reach the site of action when delivered to an animal.

Embodiments described herein relate to compositions and methods for treating heart disease and/or injury as well as to compositions and methods of promoting and/or restoring innervation or sympathetic function of myocardial tissue of a subject in need thereof. The heart disease and/or injury can be associated with or result from denervation of the heart and can include, for example, myocardial infarction, myocardial ischemia/reperfusion injury, myocardial surgery, myocardial transplantation, and/or chronic ischemia. In some embodiments, the heart disease and/or injury can include cardiac denervation hypersensitivity and arrhythmic events that can be associated with and/or result from myocardial infarction, myocardial ischemia/reperfusion injury, myocardial surgery, myocardial transplantation, and/or chronic ischemia.

It was found that following myocardial infarction resulting from, for example, acute myocardial infarction, myocardial ischemia-reperfusion injury, or chronic ischemia, sympathetic axons degenerate in and around the site of injury or infarct, leading to denervation hypersensitivity and arrhythmic events. The degeneration and subsequent lack of regeneration occurs concurrent with production of chondroitin sulfate proteoglycans (CSPGs) in the infarct. CSPGs present in the cardiac scar prevent sympathetic reinnervation by binding the neuronal protein tyrosine phosphatase receptor σ (PTPσ). It was found that targeting PTPσ with a therapeutic agent described herein, which can inhibit one or more of catalytic activity, signaling, and function of PTPσ, can promote nerve regeneration and/or restore sympathetic innervations through CSPG-containing scars in vivo in subjects and treat patients who survive a myocardial infarction and remain at risk for severe cardiac arrhythmias and sudden cardiac death. Daily injections of the therapeutic agents described herein, which target PTPσ, were sufficient to restore functional sympathetic innervation, and mitigate heterogeneity of sympathetic transmission, and reinnervation rendered hearts were surprisingly resistant to arrhythmias. Additionally, infarcted hearts with restored sympathetic innervation using the therapeutic agents described herein were found to be electrically indistinguishable from sham hearts, despite the presence of a scar. This shows that targeting PTPσ using a locally and/or systemically delivered therapeutic agent described herein in patients who have survived a myocardial infarction promotes reinnervation of otherwise denervated cardiac tissue, and that normalizing the innervation decreases arrhythmia risk.

Accordingly, in some embodiments, a method of treating and/or preventing heart disease or injury, such as myocardial infarction, myocardial ischemia/reperfusion injury, cardiac denervation hypersensitivity, and/or arrhythmic events, as well as promoting and/or restoring innervation of myocardial tissue of a subject in need thereof can include administering to the myocardial tissue of the subject a therapeutically effective amount of a composition comprising a therapeutic agent described herein, which can inhibit one or more of catalytic activity, signaling, and function of PTPσ.

In some embodiments, the subject of the disclosed method has been identified as being at risk of developing a cardiac arrhythmia. In other embodiments, the subject of the disclosed method has undergone heart surgery, including, but not limited to, open-heart surgery, heart transplantation, and minimally invasive heart surgery. In still other embodiments, the subject of the disclosed method has undergone multiple combined heart procedures, including, but not limited to, open heart procedures, heart transplantation, and minimally invasive heart surgery. In some embodiments, the subject of the disclosed method has undergone heart valve surgery and/or minimally invasive heart surgery. In some aspects, the subject of the disclosed method is at least 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, or 85 years of age. In some embodiments, the composition is administered to a subject who has had a myocardial infarction. In some aspects, the subject of the disclosed method has a history of arrhythmia.

The activity, signaling, and/or function of PTPσ can be suppressed, inhibited, and/or blocked in several ways including: direct inhibition of the activity of the intracellular domain of the PTPσ (e.g., by using small molecules, peptidomimetics, antibodies, intrabodies, or dominant negative polypeptides); activation of genes and/or proteins that inhibit one or more of, the activity, signaling, and/or function of the intracellular domain of PTPσ (e.g., by increasing the expression or activity of the genes and/or proteins); inhibition of genes and/or proteins that are downstream mediators of the PTPσ (e.g., by blocking the expression and/or activity of the mediator genes and/or proteins); introduction of genes and/or proteins that negatively regulate one or more of, activity, signaling, and/or function of PTPσ (e.g., by using recombinant gene expression vectors, recombinant viral vectors or recombinant polypeptides); or gene replacement with, for instance, a hypomorphic mutant of PTPσ (e.g., by homologous recombination, overexpression using recombinant gene expression or viral vectors, or mutagenesis).

The therapeutic agent that inhibits or reduces one or more of the activity, signaling, and/or function of PTPσ can include an agent that decreases and/or suppresses the activity, signaling, and/or function of PTPσ without inhibiting binding to or activation the LAR family phosphatases by proteoglycans, such as CSPG. Such agents can be delivered intracellularly and once delivered intracellularly promote the intrinsic growth capability of a nerve cell, such as cardiac sympathetic nerve cell, activate the growth pathway of neurons (e.g., cardiac sympathetic nerve cells), and are capable of producing a neurosalutary effect.

The neurosalutary effect can include a response or result favorable to the health or function of a neuron, of a part of the nervous system, or of the nervous system generally.

Examples of such effects include improvements in the ability of a neuron or portion of the nervous system to resist insult, to regenerate, to maintain desirable function, to grow or to survive. The neurosalutary effect can include producing or effecting such a response or improvement in function or resilience within a component of the nervous system. Examples of producing a neurosalutary effect would include stimulating axonal outgrowth after injury to a neuron; rendering a neuron resistant to apoptosis; rendering a neuron resistant to a toxic compound; reversing age-related neuronal atrophy or loss of function; reversing and/or reducing dieback, and/or promoting neural sprouting.

In some embodiments, the therapeutic agent that inhibits or reduces one or more of the activity, signaling, and/or function of PTPσ, can include a therapeutic peptide or small molecule that binds to and/or complexes with the intracellular domain of PTPσ to inhibit the activity, signaling, and/or function of PTPσ. Accordingly, therapeutic peptides or small molecules that bind to and/or complex with the intracellular domain of PTPσ of neural cells can be used to promote cell growth, motility, survival and plasticity of these cells.

The therapeutic agent can be a peptide mimetic of the wedge shaped domain (i.e., wedge domain) of the intracellular catalytic domain of PTPσ, such as described, for example, in WO 2013/155103A1, which is herein incorporated by reference in its entirety. Peptide mimetics of the wedge domain of the PTPσ when expressed in cells (e.g., neural cells) or conjugated to an intracellular transport moiety can be used to abolish PTPσ signaling in a neural cell activated with CSPG and promote cell growth, motility, and survival. Binding of these therapeutic peptides to PTPσ intact wedge domain can potentially: (i) interfere with the ability for PTPσ to interact with target proteins, such as phosphatase targets; (ii) interfere with activity promoting intermolecular interactions between PTPσ and another domain contained in PTPσ, such as the catalytically inactive second phosphatase domain D2; prevent access of proteins to the active phosphatase site; (iii) out-compete normal interactors of the wedge domain; and/or (iv) sterically inhibit phosphatase activity.

In some embodiments, the peptide mimetic (i.e., therapeutic peptide) can include, consist essentially, and/or consist of about 10 to about 20 amino acids and have an amino acid sequence that is at least about 65%, at least about 70%, at least about 75%, at least about 80%, at least about 85%, at least about 90%, at least about 95%, or about 100% homologous to an about 10 to about 20 consecutive amino acid portion of the amino acid sequence of the wedge domain of PTPσ.

A peptide (e.g., therapeutic peptide) corresponding to or substantially homologous to the wedge domain of PTPσ with a cytosolic-carrier was able to relieve CSPG-mediated inhibition, allowing neurons to advance on CSPG substrates instead of typical inhibition. This effect was dose dependent and reliant on the responding cell expressing PTPσ. This peptide can be given locally to myocardial tissue of a subject or systemically to a subject in need thereof to promote plasticity and functional recovery following dennervation of the heart.

As shown in Table 1, the wedge domain sequence of PTPσ is highly conserved among higher mammals, with only a single amino acid change in mouse and rats (Threonine to Methithione at position 6) preventing 100% homology.

TABLE 2

Wedge Domain Alignment

| 0 | | | | | | | | | 1 | | | | | | | | | | 2 | | | | | | |
|---|---|---|---|---|---|---|---|---|---|---|---|---|---|---|---|---|---|---|---|---|---|---|---|---|---|
| 1 | 2 | 3 | 4 | 5 | 6 | 7 | 8 | 9 | 0 | 1 | 2 | 3 | 4 | 5 | 6 | 7 | 8 | 9 | 0 | 1 | 2 | 3 | 4 | | |
| D | L | A | E | H | T | E | H | L | K | A | N | D | N | L | | K | | S | Q | E | Y | E | S | Xenopus | SEQ ID NO: 1 |
| D | H | T | E | H | | | L | K | A | N | D | N | L | K | L | S | Q | E | Y | E | S | I | | Green anole | SEQ ID NO: 2 |
| E | L | A | E | H | T | E | L | L | K | A | N | D | N | L | K | L | S | Q | E | Y | E | S | I | Zebrafish | SEQ ID NO: 3 |
| E | L | A | E | H | T | E | L | L | K | A | N | D | N | L | K | L | S | Q | E | Y | E | S | I | Talapia | SEQ ID NO: 4 |
| E | L | A | E | H | T | E | H | L | K | A | N | D | N | L | K | L | S | Q | E | Y | E | S | I | Chicken | SEQ ID NO: 5 |
| E | L | A | E | H | T | E | H | L | K | A | N | D | N | L | K | L | S | Q | E | Y | E | S | I | Finch | SEQ ID NO: 6 |
| E | L | A | E | H | T | D | H | L | K | A | N | D | N | L | K | L | S | Q | E | Y | E | S | I | Platypus | SEQ ID NO: 7 |
| E | M | A | E | H | T | E | H | L | K | A | N | D | N | L | K | L | S | Q | E | Y | E | S | I | Tazmanian Devil | SEQ ID NO: 8 |
| D | M | A | E | H | T | E | R | L | K | A | N | D | S | L | K | L | S | Q | E | Y | E | S | I | Ferret | SEQ ID NO: 9 |
| D | M | A | E | H | T | E | R | L | K | A | N | D | S | L | K | L | S | Q | E | Y | E | S | I | Bush-Baby | SEQ ID NO: 10 |
| D | M | A | E | H | T | E | R | L | K | A | N | D | S | L | K | L | S | Q | E | Y | E | S | I | Marmoset | SEQ ID NO: 11 |
| D | M | A | E | H | M | E | R | L | K | A | N | D | S | L | K | L | S | Q | E | Y | E | S | I | RAT | SEQ ID NO: 12 |
| D | M | A | E | H | M | E | R | L | K | A | N | D | S | L | K | L | S | Q | E | Y | E | S | I | Mouse | SEQ ID NO: 13 |
| D | M | A | E | H | T | E | R | L | K | A | N | D | S | L | K | L | S | Q | E | Y | E | S | I | Dog | SEQ ID NO: 14 |
| D | M | A | E | H | T | E | R | L | K | A | N | D | S | L | K | L | S | Q | E | Y | E | S | I | Pig | SEQ ID NO: 15 |
| D | M | A | E | H | T | E | R | L | K | A | N | D | S | L | K | L | S | Q | E | Y | E | S | I | Cow | SEQ ID NO: 16 |

TABLE 2-continued

Wedge Domain Alignment

| 1 | 2 | 3 | 4 | 5 | 6 | 7 | 8 | 9 | 0 | 1 | 2 | 3 | 4 | 5 | 6 | 7 | 8 | 9 | 0 | 1 | 2 | 3 | 4 | | |
|---|---|---|---|---|---|---|---|---|---|---|---|---|---|---|---|---|---|---|---|---|---|---|---|---|---|
| D | M | A | E | H | T | E | R | L | K | A | N | D | S | L | K | L | S | Q | E | Y | E | S | I | Sheep | SEQ ID NO: 17 |
| D | M | A | E | H | T | E | R | L | K | A | N | D | S | L | K | L | S | Q | E | Y | E | S | I | Killer Whale | SEQ ID NO: 18 |
| D | M | A | E | H | T | E | R | L | K | A | N | D | S | L | K | L | S | Q | E | Y | E | S | I | Squirrel Monkey | SEQ ID NO: 19 |
| D | M | A | E | H | T | E | R | L | K | A | N | D | S | L | K | L | S | Q | E | Y | E | S | I | Baboon | SEQ ID NO: 20 |
| D | M | A | E | H | T | E | R | L | K | A | N | D | S | L | K | L | S | Q | E | Y | E | S | I | Gorilla | SEQ ID NO: 21 |
| D | M | A | E | H | T | E | R | L | K | A | N | D | S | L | K | L | S | Q | E | Y | E | S | I | Gibbon | SEQ ID NO: 22 |
| D | M | A | E | H | T | E | R | L | K | A | N | D | S | L | K | L | S | Q | E | Y | E | S | I | Macaque | SEQ ID NO: 23 |
| D | M | A | E | H | T | E | R | L | K | A | N | D | S | L | K | L | S | Q | E | Y | E | S | I | Chimpanzee | SEQ ID NO: 24 |
| D | M | A | E | H | T | E | R | L | K | A | N | D | S | L | K | L | S | Q | E | Y | E | S | I | Human | SEQ ID NO: 25 |
| D | L | A | D | N | I | E | R | L | K | A | N | D | G | L | K | F | S | Q | E | Y | E | S | I | LAR (Lar family) | SEQ ID NO: 26 |
| E | L | A | D | H | I | E | R | L | K | A | N | D | N | L | K | F | S | Q | E | Y | E | S | I | Delta (Lar family) | SEQ ID NO: 27 |
| K | L | E | E | E | I | N | R | R | M | A | D | D | N | K | I | F | R | E | E | F | N | A | L | ptp alpha | SEQ ID NO: 28 |

As shown in Table 1, the first alpha helix of the wedge domain of PTPσ includes amino acids 1-10, the turn region includes amino acids 11-14, and the second alpha helix includes amino acids 15-24. For example, the first alpha helix of the wedge domain of human PTPσ has the amino acid sequence of DMAEHTERLK (SEQ ID NO: 29), the turn has the amino acid sequence of ANDS (SEQ ID NO: 30), and the second alpha helix has the amino acid sequence of LKLSQEYESI (SEQ ID NO: 31).

The wedge domain also shares sequence homology with the other members of the LAR family, LAR and PTPdelta. It is likely that these amino acids are necessary for the overall structure of the wedge domain. Conserved amino acids include an alanine at position 13, which marks the end of the first alpha helix and the start of the turn, making it likely to be necessary for general wedge size and structure.

Since the general secondary and tertiary structures of the wedge domain remain consistent through most receptor PTPs, several conservative substitutions can be made to a therapeutic peptide targeting the PTPσ wedge domain to obtain similar results. Examples of conservative substitutions include the substitution of one non-polar (hydrophobic) residue, such as isoleucine, valine, leucine or methionine for another, the substitution of one polar (hydrophilic) residue for another, such as between arginine and lysine, between glutamine and asparagine, between glycine and serine, the substitution of one basic residue such as lysine, arginine or histidine for another, and/or the substitution of one acidic residue, such as aspartic acid or glutamic acid for another.

These conservative substitutions can occur in the non-unique domains in either alpha helix or the turn, specifically positions 1-3 and 7-10 in the first alpha helix; 12 and 13 in the turn; and 15, 16, 18-24 in the second alpha helix. These amino acids may be necessary to the overall structure of the wedge domain, but not necessary for specificity of binding of wedge to PTPσ.

The unique amino acids to PTPσ, particularly the amino acids expressed differentially in PTPσ vs LAR, were found to be necessary for specificity of wedge domain binding. These include an EH domain in the first alpha helix position 4 and 5 followed by a threonine or a metathione (rat and mouse substitution) at position 6. In the turn, there is a unique serine at position 14 in all higher mammals. Finally, there is a unique leucine at position 17 in the second alpha helix. The potential roles of these unique amino acids will be discussed below.

The serine residue in the turn at position 14 is of particular interest due to its location in the wedge domain. This amino acid, located in the turn between alpha helixes, is slightly extended from the general secondary and tertiary structure of PTPσ, making it available for binding interactions. In addition, serine, due to its hydroxyl group and the polarity it contains, is known to facilitate several homophillic and heterophillic binding events, such as hydrogen binding between adjacent serines. Serines are also known to undergo various modifications, such as phosphorylation, making the likelihood of its necessity for specificity high. It is possible that smaller peptides that focus on the turn in the wedge domain and include the conserved serine may offer greater stability with similar function. Such peptides can be synthesized as loops, with cysteine's on either end to created di-sulfide bonds.

The unique amino acids in the first alpha helix include glutamic acid at position 4, histidine at position 5 and threonine or metathione at position 6. Although the histidine is implicated in the consensus wedge domain, it is not found in LAR, PTPdelta, PTPmu or CD45. As all three of these amino acids are either charged or polar, it is likely that either this sequence or one of its components is necessary for PTPσ wedge specificity.

Additionally, the second alpha helix contains a unique leucine at position 17. Leucines have been implicated as the critical adhesive molecules for the three dimensional structure of leucine zippers. In these molecules, which are structurally similar to wedge domains, leucines of opposing alpha helixes, located at approximately 7 intervals, interact with hydrophobic regions of the opposing alpha helix. As there is also a Leucine in the first alpha helix, located at position 9, it is believed that this unique leucine is necessary for the overall three-dimensional structural integrity of the PTPσ wedge.

Accordingly, in other embodiments, the therapeutic peptide can include, consist essentially of, or consist of about 14 to about 20 amino acids and include the amino acid sequence EHX$_1$ERLKANDSLKL (SEQ ID NO: 32), wherein X$_1$ is T or M. A therapeutic peptide including SEQ ID NO: 32 can include at least one, at least two, at least three, at least four, or at least five conservative substitutions so that the therapeutic peptide has an amino acid sequence that is at least about 65%, at least about 70%, at least about 75%, at least about 80%, at least about 85%, at least about 90%, or at least about 95% homologous to SEQ ID NO: 32.

In some embodiments, the conservative substitutions can be of amino acid residues 4E, 5R, 6L, 7K, 9N, 10D, 12L, or 13K of SEQ ID NO: 32. By way of example, amino acid residue 4E can be substituted with D or Q, amino acid residue 5R can be substituted with H, L, or K, amino acid residue 6L can be substituted with I, V, or M, amino acid residue 7K can be substituted with R or H, amino acid residue 9N can be substituted with E or D, amino acid residue 10 D can be substituted with E or N, amino acid residue 12L can be substituted with I, V, or M, and/or amino acid residue 13K can be substituted with R or H.

The therapeutic peptides described herein can be subject to other various changes, substitutions, insertions, and deletions where such changes provide for certain advantages in its use. In this regard, therapeutic peptides that bind to and/or complex with a wedge domain of PTPσ can correspond to or be substantially homologous with, rather than be identical to, the sequence of a recited polypeptide where one or more changes are made and it retains the ability to inhibits or reduces one or more of the activity, signaling, and/or function of PTPσ function.

The therapeutic polypeptide can be in any of a variety of forms of polypeptide derivatives that include amides, conjugates with proteins, cyclized polypeptides, polymerized polypeptides, analogs, fragments, chemically modified polypeptides and the like derivatives.

It will be appreciated that the conservative substitution can also include the use of a chemically derivatized residue in place of a non-derivatized residue provided that such peptide displays the requisite binding activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those polypeptides, which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides described herein also include any polypeptide having one or more additions and/or deletions or residues relative to the sequence of a polypeptide whose sequence is shown herein, so long as the requisite activity is maintained.

One or more of peptides of the therapeutic peptides described herein can also be modified by natural processes, such as posttranslational processing, and/or by chemical modification techniques, which are known in the art. Modifications may occur in the peptide including the peptide backbone, the amino acid side-chains and the amino or carboxy termini. It will be appreciated that the same type of modification may be present in the same or varying degrees at several sites in a given peptide. Modifications comprise for example, without limitation, acetylation, acylation, addition of acetomidomethyl (Acm) group, ADP-ribosylation, amidation, covalent attachment to fiavin, covalent attachment to a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycosylation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation and ubiquitination (for reference see, Protein-structure and molecular properties, 2nd Ed., T. E. Creighton, W. H. Freeman and Company, New-York, 1993).

Peptides and/or proteins described herein may also include, for example, biologically active mutants, variants, fragments, chimeras, and analogues; fragments encompass amino acid sequences having truncations of one or more amino acids, wherein the truncation may originate from the amino terminus (N-terminus), carboxy terminus (C-terminus), or from the interior of the protein. Analogues of the invention involve an insertion or a substitution of one or more amino acids. Variants, mutants, fragments, chimeras and analogues may function as inhibitors of the LAR family phosphatases (without being restricted to the present examples).

The therapeutic polypeptides described herein may be prepared by methods known to those skilled in the art. The peptides and/or proteins may be prepared using recombinant DNA. For example, one preparation can include cultivating a host cell (bacterial or eukaryotic) under conditions, which provide for the expression of peptides and/or proteins within the cell.

The purification of the polypeptides may be done by affinity methods, ion exchange chromatography, size exclusion chromatography, hydrophobicity or other purification technique typically used for protein purification. The purification step can be performed under non-denaturating conditions. On the other hand, if a denaturating step is required, the protein may be renatured using techniques known in the art.

In some embodiments, the therapeutic peptides described herein can include additional residues that may be added at either terminus of a polypeptide for the purpose of providing a "linker" by which the polypeptides can be conveniently linked and/or affixed to other polypeptides, proteins, detectable moieties, labels, solid matrices, or carriers.

Amino acid residue linkers are usually at least one residue and can be 40 or more residues, more often 1 to 10 residues. Typical amino acid residues used for linking are glycine, tyrosine, cysteine, lysine, glutamic and aspartic acid, or the like. In addition, a subject polypeptide can differ by the sequence being modified by terminal-NH2 acylation, e.g., acetylation, or thioglycolic acid amidation, by terminal-carboxylamidation, e.g., with ammonia, methylamine, and the like terminal modifications. Terminal modifications are useful, as is well known, to reduce susceptibility by proteinase digestion, and therefore serve to prolong half life of the polypeptides in solutions, particularly biological fluids where proteases may be present. In this regard, polypeptide cyclization is also a useful terminal modification, and is particularly preferred also because of the stable structures formed by cyclization and in view of the biological activities observed for such cyclic peptides as described herein.

In some embodiments, the linker can be a flexible peptide linker that links the therapeutic peptide to other polypeptides, proteins, and/or molecules, such as detectable moieties, labels, solid matrices, or carriers. A flexible peptide linker can be about 20 or fewer amino acids in length. For example, a peptide linker can contain about 12 or fewer amino acid residues, e.g., 3, 4, 5, 6, 7, 8, 9, 10, 11, and 12. In some cases, a peptide linker comprises two or more of the following amino acids: glycine, serine, alanine, and threonine.

In some embodiments, a therapeutic agent comprising the therapeutic peptides described herein can be provided in the form of a conjugate protein or drug delivery construct includes at least a transport subdomain(s) or moiety(ies) (i.e., transport moieties) that is linked to the therapeutic peptide. The transport moieties can facilitate uptake of the therapeutic polypeptides into a mammalian (i.e., human or animal) tissue or cell (e.g., neural cell). The transport moieties can be covalently linked to the therapeutic polypeptides. The covalent link can include a peptide bond or a labile bond (e.g., a bond readily cleavable or subject to chemical change in the interior target cell environment). Additionally, the transport moieties can be cross-linked (e.g., chemically cross-linked, UV cross-linked) to the therapeutic polypeptide. The transport moieties can also be linked to the therapeutic polypeptide with linking polypeptide described herein.

The transport moieties can be repeated more than once in the therapeutic agent. The repetition of a transport moiety may affect (e.g., increase) the uptake of the peptides and/or proteins by a desired cell. The transport moiety may also be located either at the amino-terminal region of therapeutic peptide or at its carboxy-terminal region or at both regions.

In one embodiment, the transport moiety can include at least one transport peptide sequence that allows the therapeutic polypeptide once linked to the transport moiety to penetrate into the cell by a receptor-independent mechanism. In one example, the transport peptide is a synthetic peptide that contains a Tat-mediated protein delivery sequence and at least one of SEQ ID NOs: 1-25 and 32. These peptides can have, respectively, the amino acid sequences of SEQ ID NOs: 33-58.

Other examples of known transport moieties, subdomains and the like are described in, for example, Canadian patent document No. 2,301,157 (conjugates containing homeodomain of antennapedia) as well as in U.S. Pat. Nos. 5,652, 122, 5,670,617, 5,674,980, 5,747,641, and 5,804,604, all of which are incorporated herein by reference in their entirety, (conjugates containing amino acids of Tat HIV protein; herpes simplex virus-1 DNA binding protein VP22, a Histidine tag ranging in length from 4 to 30 histidine repeats, or a variation derivative or homologue thereof capable of facilitating uptake of the active cargo moiety by a receptor independent process.

A 16 amino acid region of the third alpha-helix of antennapedia homeodomain has also been shown to enable proteins (made as fusion proteins) to cross cellular membranes (PCT international publication number WO 99/11809 and Canadian application No.: 2,301,157. Similarly, HIV Tat protein was shown to be able to cross cellular membranes.

In addition, the transport moiety(ies) can include polypeptides having a basic amino acid rich region covalently linked to an active agent moiety (e.g., intracellular domain-containing fragments inhibitor peptide). As used herein, the term "basic amino acid rich region" relates to a region of a protein with a high content of the basic amino acids such as arginine, histidine, asparagine, glutamine, lysine. A "basic amino acid rich region" may have, for example 15% or more of basic amino acid. In some instance, a "basic amino acid rich region" may have less than 15% of basic amino acids and still function as a transport agent region. In other instances, a basic amino acid region will have 30% or more of basic amino acids.

The transport moiety(ies) may further include a proline rich region. As used herein, the term proline rich region refers to a region of a polypeptide with 5% or more (up to 100%) of proline in its sequence. In some instance, a proline rich region may have between 5% and 15% of prolines. Additionally, a proline rich region refers to a region, of a polypeptide containing more prolines than what is generally observed in naturally occurring proteins (e.g., proteins encoded by the human genome). Proline rich regions of this application can function as a transport agent region.

In one embodiment, the therapeutic peptide described herein can be non-covalently linked to a transduction agent. An example of a non-covalently linked polypeptide transduction agent is the Chariot protein delivery system (See U.S. Pat. No. 6,841,535; *J Biol Chem* 274(35):24941-24946; and *Nature Biotec.* 19:1173-1176, all herein incorporated by reference in their entirety).

In other embodiments, the therapeutic peptides can be expressed in cells being treated using gene therapy to inhibit LAR family signaling. The gene therapy can use a vector including a nucleotide encoding the therapeutic peptides. A "vector" (sometimes referred to as gene delivery or gene transfer "vehicle") refers to a macromolecule or complex of molecules comprising a polynucleotide to be delivered to the cell. The polynucleotide to be delivered may comprise a coding sequence of interest in gene therapy. Vectors include, for example, viral vectors (such as adenoviruses (Ad), adeno-associated viruses (AAV), and retroviruses), liposomes and other lipid-containing complexes, and other macromolecular complexes capable of mediating delivery of a polynucleotide to a target cell.

Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities.

Selectable markers can be positive, negative or bifunctional. Positive selectable markers allow selection for cells carrying the marker, whereas negative selectable markers allow cells carrying the marker to be selectively eliminated. A variety of such marker genes have been described, including bifunctional (i.e., positive/negative) markers (see, e.g., Lupton, S., WO 92/08796, published May 29, 1992; and Lupton, S., WO 94/28143, published Dec. 8, 1994). Such marker genes can provide an added measure of control that can be advantageous in gene therapy contexts. A large variety of such vectors are known in the art and are generally available.

Vectors for use herein include viral vectors, lipid based vectors and other non-viral vectors that are capable of delivering a nucleotide encoding the therapeutic peptides described herein to the target cells. The vector can be a targeted vector, especially a targeted vector that preferentially binds to neurons and. Viral vectors for use in the application can include those that exhibit low toxicity to a target cell and induce production of therapeutically useful quantities of the therapeutic peptide in a cell specific manner.

Examples of viral vectors are those derived from adenovirus (Ad) or adeno-associated virus (AAV). Both human and non-human viral vectors can be used and the recombinant viral vector can be replication-defective in humans. Where the vector is an adenovirus, the vector can comprise a polynucleotide having a promoter operably linked to a gene encoding the therapeutic peptides and is replication-defective in humans.

Other viral vectors that can be used herein include herpes simplex virus (HSV)-based vectors. HSV vectors deleted of one or more immediate early genes (IE) are advantageous because they are generally non-cytotoxic, persist in a state similar to latency in the target cell, and afford efficient target cell transduction. Recombinant HSV vectors can incorporate approximately 30 kb of heterologous nucleic acid.

Retroviruses, such as C-type retroviruses and lentiviruses, might also be used in the application. For example, retroviral vectors may be based on murine leukemia virus (MLV). See, e.g., Hu and Pathak, Pharmacol. Rev. 52:493-511, 2000 and Fong et al., Crit. Rev. Ther. Drug Carrier Syst. 17:1-60, 2000. MLV-based vectors may contain up to 8 kb of heterologous (therapeutic) DNA in place of the viral genes. The heterologous DNA may include a tissue-specific promoter and a nucleic acid encoding the therapeutic peptide. In methods of delivery to neural cells, it may also encode a ligand to a tissue specific receptor.

Additional retroviral vectors that might be used are replication-defective lentivirus-based vectors, including human immunodeficiency (HIV)-based vectors. See, e.g., Vigna and Naldini, J. Gene Med. 5:308-316, 2000 and Miyoshi et al., J. Virol. 72:8150-8157, 1998. Lentiviral vectors are advantageous in that they are capable of infecting both actively dividing and non-dividing cells.

Lentiviral vectors for use in the application may be derived from human and non-human (including SIV) lentiviruses. Examples of lentiviral vectors include nucleic acid sequences required for vector propagation as well as a tissue-specific promoter operably linked to a therapeutic peptide encoding nucleic acid. These former may include the viral LTRs, a primer binding site, a polypurine tract, att sites, and an encapsidation site.

In some aspects, a lentiviral vector can be employed. Lentiviruses have proven capable of transducing different types of CNS neurons (Azzouz et al., (2002) J Neurosci. 22: 10302-12) and may be used in some embodiments because of their large cloning capacity.

A lentiviral vector may be packaged into any lentiviral capsid. The substitution of one particle protein with another from a different virus is referred to as "pseudotyping". The vector capsid may contain viral envelope proteins from other viruses, including murine leukemia virus (MLV) or vesicular stomatitis virus (VSV). The use of the VSV G-protein yields a high vector titer and results in greater stability of the vector virus particles.

Alphavirus-based vectors, such as those made from semliki forest virus (SFV) and sindbis virus (SIN) might also be used in the application. Use of alphaviruses is described in Lundstrom, K., Intervirology 43:247-257, 2000 and Perri et al., Journal of Virology 74:9802-9807, 2000.

Recombinant, replication-defective alphavirus vectors are advantageous because they are capable of high-level heterologous (therapeutic) gene expression, and can infect a wide target cell range. Alphavirus replicons may be targeted to specific cell types by displaying on their virion surface a functional heterologous ligand or binding domain that would allow selective binding to target cells expressing a cognate binding partner. Alphavirus replicons may establish latency, and therefore long-term heterologous nucleic acid expression in a target cell. The replicons may also exhibit transient heterologous nucleic acid expression in the target cell.

In many of the viral vectors compatible with methods of the application, more than one promoter can be included in the vector to allow more than one heterologous gene to be expressed by the vector. Further, the vector can comprise a sequence, which encodes a signal peptide or other moiety, which facilitates expression of the therapeutic peptide from the target cell.

To combine advantageous properties of two viral vector systems, hybrid viral vectors may be used to deliver a nucleic acid encoding a therapeutic peptide to a target neuron, cell, or tissue. Standard techniques for the construction of hybrid vectors are well-known to those skilled in the art. Such techniques can be found, for example, in Sambrook, et al., In Molecular Cloning: A laboratory manual. Cold Spring Harbor, N.Y. or any number of laboratory manuals that discuss recombinant DNA technology. Double-stranded AAV genomes in adenoviral capsids containing a combination of AAV and adenoviral ITRs may be used to transduce cells. In another variation, an AAV vector may be placed into a "gutless", "helper-dependent" or "high-capacity" adenoviral vector. Adenovirus/AAV hybrid vectors are discussed in Lieber et al., J. Virol. 73:9314-9324, 1999. Retrovirus/adenovirus hybrid vectors are discussed in Zheng et al., Nature Biotechnol. 18:176-186, 2000. Retroviral genomes contained within an adenovirus may integrate within the target cell genome and effect stable gene expression.

Other nucleotide sequence elements, which facilitate expression of the therapeutic peptide and cloning of the vector are further contemplated. For example, the presence of enhancers upstream of the promoter or terminators downstream of the coding region, for example, can facilitate expression.

In accordance with another embodiment, a tissue-specific promoter can be fused to nucleotides encoding the therapeutic peptides described herein. By fusing such tissue specific promoter within the adenoviral construct, transgene expression is limited to a particular tissue. The efficacy of gene expression and degree of specificity provided by tissue specific promoters can be determined, using the recombinant adenoviral system of the present application. Neuron specific promoters, such as the platelet-derived growth factor β-chain (PDGF-β) promoter and vectors, are well known in the art.

In addition to viral vector-based methods, non-viral methods may also be used to introduce a nucleic acid encoding a therapeutic peptide into a target cell. A review of non-viral methods of gene delivery is provided in Nishikawa and Huang, Human Gene Ther. 12:861-870, 2001. An example of a non-viral gene delivery method according to the application employs plasmid DNA to introduce a nucleic acid encoding a therapeutic peptide into a cell. Plasmid-based gene delivery methods are generally known in the art.

Synthetic gene transfer molecules can be designed to form multimolecular aggregates with plasmid DNA. These aggregates can be designed to bind to a target cell. Cationic amphiphiles, including lipopolyamines and cationic lipids, may be used to provide receptor-independent nucleic acid transfer into target cells.

In addition, preformed cationic liposomes or cationic lipids may be mixed with plasmid DNA to generate cell-transfecting complexes. Methods involving cationic lipid formulations are reviewed in Felgner et al., Ann. N.Y. Acad. Sci. 772:126-139, 1995 and Lasic and Templeton, Adv. Drug Delivery Rev. 20:221-266, 1996. For gene delivery, DNA may also be coupled to an amphipathic cationic peptide (Fominaya et al., J. Gene Med. 2:455-464, 2000).

Methods that involve both viral and non-viral based components may be used according to the application. For example, an Epstein Barr virus (EBV)-based plasmid for therapeutic gene delivery is described in Cui et al., Gene Therapy 8:1508-1513, 2001. Additionally, a method involving a DNA/ligand/polycationic adjunct coupled to an adenovirus is described in Curiel, D. T., Nat. Immun. 13:141-164, 1994.

Additionally, the nucleic acid encoding the therapeutic peptides can be introduced into the target cell by transfecting the target cells using electroporation techniques. Electroporation techniques are well known and can be used to facilitate transfection of cells using plasmid DNA.

Vectors that encode the expression of the therapeutic peptides can be delivered in vivo to the target cell in the form of an injectable preparation containing pharmaceutically acceptable carrier, such as saline, as necessary. Other pharmaceutical carriers, formulations and dosages can also be used in accordance with the present application.

Where the target cell includes a cardiac nerve cell being treated, such as sympathetic cardiac nerves, the vector can be delivered by direct injection into or about the periphery of the neuron at an amount sufficient for the therapeutic peptide to be expressed to a degree, which allows for highly effective therapy. By injecting the vector directly into or about the periphery of the neuron, it is possible to target the vector transfection rather effectively, and to minimize loss of the recombinant vectors. This type of injection enables local transfection of a desired number of cells, especially at a site of infarction or injury injury, thereby maximizing therapeutic efficacy of gene transfer, and minimizing the possibility of an inflammatory response to viral proteins. Other methods of administering the vector to the target cells can be used and will depend on the specific vector employed.

The therapeutic peptide can be expressed for any suitable length of time within the target cell, including transient expression and stable, long-term expression. In one aspect of the application, the nucleic acid encoding the therapeutic peptide will be expressed in therapeutic amounts for a defined length of time effective to induce activity and growth of the transfected cells. In another aspect of the application, the nucleic acid encoding the therapeutic peptide will be expressed in therapeutic amounts for a defined length of time effective to restore sympathetic innervation to the myocardial tissue.

The therapeutic agents described herein may be modified (e.g., chemically modified). Such modification may be designed to facilitate manipulation or purification of the molecule, to increase solubility of the molecule, to facilitate administration, targeting to the desired location, to increase or decrease half life. A number of such modifications are known in the art and can be applied by the skilled practitioner.

In the methods of treatment disclosed herein, a therapeutically effective amount of the therapeutic agent is administered to the subject to treat the heart disease and/or injury and/or promote and/or restore innervation or sympathetic function of myocardial tissue of a subject in need thereof. In one embodiment, a formulation including the therapeutic agent can be administered to the subject in the period from the time of, for example, an injury to the myocardial tissue up to hours, days, and/or weeks after the injury has occurred, for example within 24 hours, several days, or weeks from the time of injury.

The therapeutic agents can be delivered to a subject by any suitable route, including, for example, local and/or systemic administration. Systemic administration can include, for example, parenteral administration, such as intramuscular, intravenous, intraarticular, intraarterial, intrathecal, subcutaneous, or intraperitoneal administration. The agent can also be administered orally, transdermally, topically, by inhalation (e.g., intrabronchial, intranasal, oral inhalation or intranasal drops) or rectally. In some embodiments, the therapeutic agent can be administered to the subject via intravenous administration using an infusion pump to deliver daily, weekly, or doses of the therapeutic agent.

Desirable features of local administration include achieving effective local concentrations of the therapeutic agent as well as avoiding adverse side effects from systemic administration of the therapeutic agent. In one embodiment, the therapeutic agent can be introduced directly into the cardiac tissue.

Pharmaceutically acceptable formulations of the therapeutic agent can be suspended in aqueous vehicles and introduced through conventional hypodermic needles or using infusion pumps.

For injection, therapeutic agent can be formulated in liquid solutions, typically in physiologically compatible buffers such as Hank's solution or Ringer's solution. In addition, the therapeutic agent may be formulated in solid form and re-dissolved or suspended immediately prior to use. Lyophilized forms are also included. The injection can be, for example, in the form of a bolus injection or continuous infusion (such as using infusion pumps) of the therapeutic agent.

In some embodiments, the therapeutic agent can be administered to a weakened region, ischemic region, and/or peri-infarct region of the myocardial tissue by direct injection of the therapeutic agent into or about the periphery the weakened region, ischemic region, and/or peri-infarct region of the myocardial tissue at an amount effective to promote and/or restore functional sympathetic innervation of the myocardial tissue, reduce arrhythmic susceptibility, normalize electrophysiology of the myocardial tissue, and/or mitigate heterogeneity of sympathetic transmission of the myocardial tissue. By injecting the therapeutic agent directly into or about the periphery of the weakened region, ischemic region, and/or peri-infarct region of the myocardial tissue, it is possible to target the therapeutic agent to the tissue. This can enable local delivery to and/or transduction of a desired number of cells, especially about the weakened region, ischemic region, and/or peri-infarct region of the myocardial tissue, thereby maximizing therapeutic efficacy of protein transduction or gene transfer, and minimizing the possibility of an inflammatory response.

It will be appreciated that the amount, volume, concentration, and/or dosage of the therapeutic agent that is administered to any one animal or human depends on many factors, including the subject's size, body surface area, age, the particular composition to be administered, sex, time and route of administration, general health, and other drugs being administered concurrently. Specific variations of the above noted amounts, volumes, concentrations, and/or dosages of therapeutic agent can be readily be determined by one skilled in the art using the experimental methods described below.

In some embodiments, a therapeutic agent, such as a therapeutic peptide described herein, can be administered can be administered locally and/or systemically to a subject in need thereof at a dose or amount of about 0.1 µmol, about 1 µmol, about 5 µmol, about 10 µmol, or more; or about 0.0001 mg/kg, about 0.001 mg/kg, about 0.01 mg/kg, about 0.1 mg/kg, or about 1 mg/kg to about 5 mg/kg or 10 mg/kg of the subject being treated. The therapeutic agent can be administered daily, weekly, biweekly, monthly or less frequently until there is maximal innervation of the heart scar region, peri-infact region, or infarct region to re-innervate surviving penumbral cardiomyocytes and any left in islands from deeply within the heart scar.

In some embodiments, the therapeutic agent can be administered by direct injection using catheterization, such as endo-ventricular catheterization or intra-myocardial catheterization. In one example, a deflectable guide catheter device can be advanced to a left ventricle retrograde across the aortic valve. Once the device is positioned in the left ventricle, the therapeutic agent can be injected into the peri-infarct region (both septal and lateral aspect) area of the left ventricle.

The myocardial tissue of the subject can be imaged prior to administration of the therapeutic agent to define the area of weakened, ischemic, and/or peri-infarct region prior to administration of the therapeutic agent. Defining the weakened, ischemic, and/or peri-infarct region by imaging allows for more accurate intervention and targeting of the therapeutic agent to the weakened, ischemic, and/or peri-infarct region. The imaging technique used to define the weakened, ischemic, and/or peri-infarct region of the myocardial tissue can include any known cardio-imaging technique. Such imaging techniques can include, for example, at least one of echocardiography, magnetic resonance imaging, coronary angiogram, electroanatomical mapping, or fluoroscopy. It will be appreciated that other imaging techniques that can define the weakened, ischemic, and/or peri-infarct region can also be used.

In another embodiment, the therapeutic agent can be administered to a subject systemically by intravenous injection or locally at the site of injury, usually within about 24 hours, about 48 hours, about 100 hours, or about 200 hours or more of when an injury occurs (e.g., within about 6 hours, about 12 hours, or 24 hours, inclusive, of the time of the injury).

In some embodiments, the therapeutic agent can administered to a subject for an extended period of time to promote innervation of the infarct tissue as well as inhibit, ameliorate, and/or reduce arrhythmias in the heart of the subject. Sustained contact with the therapeutic agent can be achieved, for example, by repeated administration of the active compound(s) over a period of time, such as one week, several weeks, one month or longer.

In other embodiments, a pharmaceutically acceptable formulation used to administer the therapeutic agent(s) can also be formulated to provide sustained delivery of the active compound to a subject. For example, the formulation may deliver the active compound for at least one, two, three, or four weeks, inclusive, following initial administration to the subject. For example, a subject to be treated in accordance with the method described herein can be treated with the therapeutic agent for at least 30 days (either by repeated administration or by use of a sustained delivery system, or both).

Sustained delivery of the therapeutic agent can be demonstrated by, for example, the continued therapeutic effect of the therapeutic agent over time (such as sustained delivery of the agents can be demonstrated by continued inhibitions of arrhythmias in a subject). Alternatively, sustained delivery of the therapeutic agent may be demonstrated by detecting the presence of the therapeutic agents in vivo over time.

Approaches for sustained delivery include use of a polymeric capsule, a minipump to deliver the formulation, a biodegradable implant, or implanted transgenic autologous cells (see U.S. Pat. No. 6,214,622). Implantable infusion pump systems (e.g., INFUSAID pumps (Towanda, Pa.)); see Zierski et al., 1988; Kanoff, 1994) and osmotic pumps (sold by Alza Corporation) are available commercially and otherwise known in the art. Another mode of administration is via an implantable, externally programmable infusion pump. Infusion pump systems and reservoir systems are also described in, e.g., U.S. Pat. No. 5,368,562 and U.S. Pat. No. 4,731,058.

Vectors encoding the therapeutic peptides can often be administered less frequently than other types of therapeutics. For example, an effective amount of such a vector can range from about 0.01 mg/kg to about 5 or 10 mg/kg, inclusive; administered daily, weekly, biweekly, monthly or less frequently.

The ability to deliver or express the therapeutic peptides allows for cell activity modulation in a number of different cell types. The therapeutic peptides can be expressed, for example, in a heart cell via heart specific promoters for modulating the contractions (or excitability) of the heart.

In some embodiment, the efficacy of the therapeutic polypeptides in treating heart disease and/or injury as well as promoting and/or restoring innervation or sympathetic function of myocardial tissue of a subject in need thereof can be measured using, for example, electrocardiogram (ECG) monitoring to determine the electrophysiology of the heart. The ECG measurements can be compared to normal or control ECG measurements to determine efficacy of the therapeutic agent in normalizing or restoring electrophysiology of the heart. In some embodiments, ECG can be used in a conjunction with a cardiac stress test or with telemetry to determine efficacy of therapeutic agent in promoting or restoring cardiac innervation or sympathetic function in the myocardial tissue. It will be appreciated that other tests used to measure cardiac electrophysiology and arrhythmic onset can be used to measure efficacy of the therapeutic agents.

It is further contemplated herein that enzymatically, for example, via chondroitinase: ChABC, modifying inhibitory extracellular matrices in the infarct combined with administration of the therapeutic agents can maximize the sprouting capacity and functional impact of remaining nerve fibers. It is further contemplated that enhancing and/or bringing about much greater total fiber sprouting combined with enhancing the physiological output of the neurons themselves will act synergistically to treat the heart injury or disease. Therefore, in another embodiment, subjects can be administered chondroitinase ABC in addition to the therapeutic agents described herein to bring about an even more enhanced recovery than either treatment used alone. In some embodiments, bolus injections of ChABC into the vicinity of a infarct can promote innervation in the infarct in a subject.

In other embodiments, the therapeutic agents described herein can be administered in combination with a second agent to treat the heart disease or injury. The term "in combination with" a second agent or treatment includes co-administration of the therapeutic agent described herein (e.g., therapeutic peptide described herein) with the second agent or treatment, administration of the therapeutic agent described herein first, followed by the second agent or treatment and administration of the second agent or treatment first, followed by the therapeutic agent described herein.

The term "second agent" includes any agent which is known in the art to treat, prevent, or reduce the symptoms of a heart disease or injury including for example, acute decompensated heart failure (ADHF), chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, obesity, peripheral arterial disease, cerebrovascular accidents, transient ischemic attacks, ischemic reperfusion injury.

Examples of second agents include inotropes, beta adrenergic receptor blockers, HMG-Co-A reductase inhibitors, angiotensin II receptor antagonists, angiotensin converting enzyme (ACE) Inhibitors, calcium channel blockers (CCB), endothelin antagonists, renin inhibitors, diuretics, ApoA-I mimics, anti-diabetic agents, obesity-reducing agents, aldosterone receptor blockers, endothelin receptor blockers, aldosterone synthase inhibitors (ASI), a CETP inhibitor, anti-coagulants, relaxin, BNP (nesiritide) and/or a NEP inhibitor.

Inotropes as used herein include, for example, dobutamine, isoproterenol, milrinone, amirinone, levosimendan, epinephrine, norepinephrine, isoproterenol and digoxin.

Beta adrenergic receptor blockers as used herein include, for example, acebutolol, atenolol, betaxolol, bisoprolol, carteolol, metoprolol, nadolol, propranolol, sotalol and timolol.

Anti-coagulants as used herein include Dalteparin, Danaparoid, Enoxaparin, Heparin, Tinzaparin, Warfarin.

The term "HMG-Co-A reductase inhibitor" (also called beta-hydroxy-beta-methylglutaryl-co-enzyme-A reductase inhibitors) includes active agents that may be used to lower the lipid levels including cholesterol in blood. Examples include atorvastatin, cerivastatin, compactin, dalvastatin, dihydrocompactin, fluindostatin, fluvastatin, lovastatin, pitavastatin, mevastatin, pravastatin, rosuvastatin, rivastatin, simvastatin, and velostatin, or, pharmaceutically acceptable salts thereof.

The term "ACE-inhibitor" (also called angiotensin converting enzyme inhibitors) includes molecules that interrupt the enzymatic degradation of angiotensin I to angiotensin II. Such compounds may be used for the regulation of blood pressure and for the treatment of congestive heart failure. Examples include alacepril, benazepril, benazeprilat, captopril, ceronapril, cilazapril, delapril, enalapril, enaprilat, fosinopril, imidapril, lisinopril, moexipril, moveltopril, perindopril, quinapril, ramipril, spirapril, temocapril, and trandolapril, or, pharmaceutically acceptables salt thereof.

The term "endothelin antagonist" includes bosentan (cf. EP 526708 A), tezosentan (cf. WO 96/19459), or, pharmaceutically acceptable salts thereof.

The term "renin inhibitor" includes ditekiren; terlakiren; Aliskiren, or, hydrochloride salts thereof, or, SPP630, SPP635 and SPP800 as developed by Speedel, or RO 66-1132 and RO 66-1168 or, pharmaceutically acceptable salts thereof. The term "aliskiren", if not defined specifically, is to be understood both as the free base and as a salt thereof, especially a pharmaceutically acceptable salt thereof, most preferably a hemi-fumarate salt thereof.

The term "calcium channel blocker (CCB)" includes dihydropyridines (DHPs) and non-DHPs (e.g., diltiazem-type and verapamil-type GCBs). Examples include amlodipine, Bepridil, Diltiazem, felodipine, ryosidine, isradipine, lacidipine, nicardipine, nifedipine, niguldipine, niludipine, nimodipine, nisoldipine, nitrendipine, Verapamil and nivaldipine, and is preferably a non-DHP representative selected from the group consisting of flunarizine, prenylamine, diltiazem, fendiline, gallopamil, mibefradil, anipamil, tiapamil and verapamil, or, pharmaceutically acceptable salts thereof. CCBs may be used as antihypertensive, anti-angina pectoris, or anti-arrhythmic drugs.

The term "diuretic" includes thiazide derivatives (e.g., chlorothiazide, hydrochlorothiazide, methylclothiazide, and chlorothalidon).

An angiotensin II receptor antagonist or a pharmaceutically acceptable salt thereof is understood to be an active ingredient which bind to the $AT_1$-receptor subtype of angiotensin II receptor but do not result in activation of the receptor. As a consequence of the inhibition of the AT1 receptor, these antagonists can, for example, be employed as antihypertensives or for treating congestive heart failure.

The term "anti-diabetic agent" includes insulin secretion enhancers that promote the secretion of insulin from pancreatic β-cells. Examples include biguanide derivatives (e.g., metformin), sulfonylureas (SU) (e.g., tolbutamide, chlorpropamide, tolazamide, acetohexamide, 4-chloro-N-[(1-pyrrolidinylamino)carbonyl]-benzensulfonamide (glycopyramide), glibenclamide (glyburide), gliclazide, 1-butyl-3-metanilylurea, carbutamide, glibonuride, glipizide, gliquidone, glisoxepid, glybuthiazole, glibuzole, glyhexamide, glymidine, glypinamide, phenbutamide, and tolylcyclamide), or pharmaceutically acceptable salts thereof. Further examples include phenylalanine derivatives (e.g., nateglinide [N-(trans-4-isopropylcyclohexylcarbonyl)-D-phenylalanine], repaglinide; calcium (2S)-2-benzyl-3-(cis-hexahydro-2-isoindolinlycarbonyl)-propionate dihydrate; and glimepiride.

Further examples of second agents with which the peptide and polypeptide of the invention can be used in combination include DPP-IV inhibitors, GLP-1 and GLP-1 agonists.

DPP-IV is responsible for inactivating GLP-1. More particularly, DPP-IV generates a GLP-1 receptor antagonist and thereby shortens the physiological response to GLP-1. GLP-1 is a major stimulator of pancreatic insulin secretion and has direct beneficial effects on glucose disposal.

The DPP-IV (dipeptidyl peptidase IV) inhibitor can be peptidic or, preferably, non-peptidic. DPP-IV inhibitors are in each case generically and specifically disclosed, e.g., in WO 98/19998, DE 196 16 486 A1, WO 00/34241 and WO 95/15309, in each case in particular in the compound claims and the final products of the working examples, the subject-matter of the final products, the pharmaceutical preparations and the claims are hereby incorporated into the present application by reference to these publications. Preferred are those compounds that are specifically disclosed in Example 3 of WO 98/19998 and Example 1 of WO 00/34241, respectively.

GLP-1 (glucagon like peptide-1) is an insulinotropic protein, which is described, e.g., by W. E. Schmidt et al. in Diabetologia, 28, 1985, 704-707 and in U.S. Pat. No. 5,705,483.

The term "GLP-1 agonists" includes variants and analogs of GLP-1(7-36)$NH_2$, which are disclosed in particular in U.S. Pat. Nos. 5,120,712, 5,118,666, 5,512,549, WO 91/11457 and by C. Orskov et al in J. Biol. Chem. 264 (1989) 12826.

Also included in the definition "anti-diabetic agent" are insulin sensitivity enhancers which restore impaired insulin receptor function to reduce insulin resistance and consequently enhance the insulin sensitivity. Examples include hypoglycemic thiazolidinedione derivatives (e.g., glitazone, (S)-((3,4-dihydro-2-(phenyl-methyl)-2H-1-benzopyran-6-yl)methyl-thiazolid-ine-2,4-dione (englitazone), 5-{[4-(3-(5-methyl-2-phenyl-4-oxazolyl)-1-oxopropyl)-phenyl]-methyl}-thia-zolidine-2,4-dione (darglitazone), 5-{[4-(1-methyl-cyclohexyl)methoxy)-phenyl]methyl}-thiazolidine-2,4-dione (ciglitazone), 5-{[4-(2-(1-indolyl)ethoxy)phenyl]methyl}-thiazolidine-2,4-dione (DRF2189), 5-{4-[2-(5-methyl-2-phenyl-4-oxazolyl)-ethoxy)]benzyl}-thiazolidine-2,4-d-ione (BM-13.1246), 5-(2-naphthylsulfonyl)-thiazolidine-2,4-dione (AY-31637), bis{4-[(2,4-dioxo-5-thiazolidinyl)methyl]phenyl}methane (YM268), 5-{4-[2-(5-methyl-2-phenyl-4-oxazolyl)-2-hydroxyethoxy]benzyl}-t-hiazolidine-2,4-dione (AD-5075), 5-[4-(1-phenyl-1-cyclopropanecarbonylamino)-benzyl]-thiazolidine-2,4-dion-e (DN-108) 5-{[4-(2-(2,3-dihydroindol-1-yl)ethoxy)phenyl]methyl}-thiazolid-ine-2,4-dione, 5-[3-(4-chloro-phenyl])-2-propynyl]-5-phenylsulfonyl)thiazolidine-2,4-dio-ne, 5-[3-(4-chlorophenyl])-2-propynyl]-5-(4-fluorophenyl-sulfonyl)thiazoli-dine-2,4-dione, 5-{[4-(2-(methyl-2-pyridinyl-amino)-ethoxy)phenyl]methyl}-thiazolidine-2,-4-dione (rosiglitazone), 5-{[4-(2-(5-ethyl-2-pyridyl)ethoxy)phenyl]-methyl}thiazolidine-2,4-dione (pioglitazone), 5-{[4-((3,4-dihydro-6-hydroxy-2,5,7,8-tetramethyl-2H-1-benzopyran-2-yl)me-thoxy)-phenyl]-methyl}-thiazolidine-2,4-dione (troglitazone), 5-[6-(2-fluoro-benzyloxy)naphthalen-2-ylmethyl]-thiazolidine-2,4-dione (MCC555), 5-{[2-(2-naphthyl)-benzoxazol-5-yl]-methyl}thiazolidine-2,4-dio-ne (T-174) and 5-(2,4-dioxothiazolidin-5-ylmethyl)-2-methoxy-N-(4-trifluoromethyl-benzyl-)benzamide (KRP297)).

Further anti-diabetic agents include, insulin signalling pathway modulators, like inhibitors of protein tyrosine phosphatases (PTPases), antidiabetic non-small molecule mimetic compounds and inhibitors of glutamine-fructose-6-phosphate amidotransferase (GFAT); compounds influencing a dysregulated hepatic glucose production, like inhibitors of glucose-6-phosphatase (G6Pase), inhibitors of fructose-1,6-bisphosphatase (F-1,6-Bpase), inhibitors of glycogen phosphorylase (GP), glucagon receptor antagonists and inhibitors of phosphoenolpyruvate carboxykinase (PEPCK); pyruvate dehydrogenase kinase (PDHK) inhibitors; inhibitors of gastric emptying; insulin; inhibitors of GSK-3; retinoid X receptor (RXR) agonists; agonists of Beta-3 AR; agonists of uncoupling proteins (UCPs); non-glitazone type PPARδ agonists; dual PPARα/PPARδ agonists; antidiabetic vanadium containing compounds; incretin hormones, like glucagon-like peptide-1 (GLP-1) and GLP-1 agonists; beta-cell imidazoline receptor antagonists; miglitol; $α_2$-adrenergic antagonists; and pharmaceutically acceptable salts thereof.

The term "obesity-reducing agent" includes lipase inhibitors (e.g., orlistat) and appetite suppressants (e.g., sibutramine and phentermine).

An aldosterone synthase inhibitor or a pharmaceutically acceptable salt thereof is understood to be an active ingredient that has the property to inhibit the production of aldosterone. Aldosterone synthase (CYP11B2) is a mitochondrial cytochrome P450 enzyme catalyzing the last step of aldosterone production in the adrenal cortex, i.e., the conversion of 11-deoxycorticosterone to aldosterone. The inhibition of the aldosterone production with so-called aldosterone synthase inhibitors is known to be a successful variant to treatment of hypokalemia, hypertension, congestive heart failure, atrial fibrillation or renal failure. Such aldosterone synthase inhibition activity is readily determined by those skilled in the art according to standard assays (e.g., US 2007/0049616).

The class of aldosterone synthase inhibitors comprises both steroidal and non-steroidal aldosterone synthase inhibitors, the later being most preferred. The class of aldosterone synthase inhibitors comprises compounds having differing structural features. An example of non-steroidal aldosterone synthase inhibitor is the (+)-enantiomer of the hydrochloride of fadrozole (U.S. Pat. Nos. 4,617,307 and 4,889,861)

Aldosterone synthase inhibitors include, without limitation 4-(6,7-dihydro-5H-pyrrolo[1,2-c]imidazol-5-yl)-3-methylbenzonitrile; 5-(2-chloro-4-cyanophenyl)-6,7-dihydro-5H-pyrrolo[1,2-c]imidazole-5-carbo-xylic acid (4-methoxybenzyl)methylamide; 4'-fluoro-6-(6,7,8,9-tetrahydro-5H-imidazo[1,5-a]azepin-5-yl)biphenyl-3-c-arbonitrile; 5-(4-Cyano-2-methoxyphenyl)-6,7-dihydro-5H-pyrrolo[1,2-c]imidazole-5-carb-oxylic acid butyl ester; 4-(6,7-Dihydro-5H-pyrrolo[1,2-c]imidazol-5-yl)-2-methoxybenzonitrile; 5-(2-Chloro-4-cyanophenyl)-6,7-dihydro-5H-pyrrolo[1,2-c]imidazole-5-carbo-xylic acid 4-fluorobenzyl ester; 5-(4-Cyano-2-trifluoromethoxyphenyl)-6,7-dihydro-5H-pyrrolo[1,2-c]imidazo-le-5-carboxylic acid methyl ester; 5-(4-Cyano-2-methoxyphenyl)-6,7-dihydro-5H-pyrrolo[1,2-c]imidazole-5-carb-oxylic acid 2-isopropoxyethyl ester; 4-(6,7-Dihydro-5H-pyrrolo[1,2-c]imidazol-5-yl)-2-methylbenzonitrile; 4-(6,7-dihydro-5H-pyrrolo[1,2-c]imidazol-5-yl)-3-fluorobenzonitrile; 4-(6,7-Dihydro-5H-pyrrolo[1,2-c]imidazol-5-yl)-2-methoxybenzonitrile; 3-Fluoro-4-(7-methylene-6,7-dihydro-5H-pyrrolo[1,2-c]imidazol-5-yl)benzon-itrile; cis-3-Fluoro-4-[7-(4-fluoro-benzyl)-5,6,7,8-tetrahydro-imidazo[1,5--a]pyridin-5-yl]benzonitrile; 4'-Fluoro-6-(9-methyl-6,7,8,9-tetrahydro-5H-imidazo[1,5-a]azepin-5-yl)bip-henyl-3-carbonitrile; 4'-Fluoro-6-(9-methyl-6,7,8,9-tetrahydro-5H-imidazo[1,5-a]azepin-5-yl)biphenyl-3-carbonitrile or in each case, the (R) or (S) enantiomer thereof; or if appropriable, a pharmaceutically acceptable salt thereof.

The term aldosterone synthase inhibitors also include compounds and analogs disclosed in WO2008/076860, WO2008/076336, WO2008/076862, WO2008/027284, WO2004/046145, WO2004/014914, WO2001/076574.

Furthermore Aldosterone synthase inhibitors also include compounds and analogs disclosed in U.S. patent applications US2007/0225232, US2007/0208035, US2008/0318978, US2008/0076794, US2009/0012068, US20090048241 and in PCT applications WO2006/005726, WO2006/128853, WO2006128851, WO2006/128852, WO2007065942, WO2007/116099, WO2007/116908, WO2008/119744 and in European patent application EP 1886695. Preferred aldosterone synthase inhibitors suitable for use in the present invention include, without limitation 8-(4-Fluorophenyl)-5,6-dihydro-8H-imidazo[5, 1-c][1,4]oxazine; 4-(5,6-Dihydro-8H-imidazo[5, 1-c][1,4]oxazin-8-yl)-2-fluorobenzonitrile; 4-(5,6-Dihydro-8H-imidazo[5,1-c][1,4]oxazin-8-yl)-2,6-difluorobenzonitril-e; 4-(5,6-Dihydro-8H-imidazo[5,1-c][1,4]oxazin-8-yl)-2-methoxybenzonitrile-; 3-(5,6-Dihydro-8H-imidazo[5,1-c][1,4]oxazin-8-yl)benzonitrile; 4-(5,6-Dihydro-8H-imidazo[5,1-c][1,4]oxazin-8-yl)phthalonitrile; 4-(8-(4-Cyanophenyl)-5,6-dihydro-8H-imidazo[5,1-c][1,4]oxazin-8-yl)benzon-itrile; 4-(5,6-Dihydro-8H-imidazo[5,1-c][1,4]oxazin-8-yl)benzonitrile; 4-(5,6-Dihydro-8H-imidazo[5,1-c][1,4]oxazin-8-yl)naphthalene-1-carbonitri-le; 8-[4-(1H-Tetrazol-5-yl)phenyl]-5,6-dihydro-8H-imidazo[5,1-c][1,4]oxazi-ne as developed by Speedel or in each case, the (R) or (S) enantiomer thereof; or if appropriable, a pharmaceutically acceptable salt thereof.

The term "endothelin receptor blocker" includes bosentan and ambrisentan.

The term "CETP inhibitor" refers to a compound that inhibits the cholesteryl ester transfer protein (CETP) mediated transport of various cholesteryl esters and triglycerides from HDL to LDL and VLDL. Such CETP inhibition activity is readily determined by those skilled in the art according to standard assays (e.g., U.S. Pat. No. 6,140,343). Examples include compounds disclosed in U.S. Pat. No. 6,140,343 and U.S. Pat. No. 6,197,786 (e.g., [2R,4S]4-[(3, 5-bis-trifluoromethyl-benzyl)-methoxycarbonyl-amino]-2-ethyl-6-trifluoromethyl-3,4-dihydro-2H-quinoline-1-carboxylic acid ethyl ester (torcetrapib); compounds disclosed in U.S. Pat. No. 6,723,752 (e.g., (2R)-3-{[3-(4-Chloro-3-ethyl-phenoxy)-phenyl]-[[3-(1,1,2,2-tetrafluoro-et-hoxy)-phenyl]-methyl]-amino}-1,1,1-trifluoro-2-propanol); compounds disclosed in U.S. patent application Ser. No. 10/807, 838; polypeptide derivatives disclosed in U.S. Pat. No. 5,512,548; rosenonolactone derivatives and phosphate-containing analogs of cholesteryl ester disclosed in J. Antibiot, 49(8): 815-816 (1996), and Bioorg. Med. Chem. Lett.; 6:1951-1954 (1996), respectively. Furthermore, the CETP inhibitors also include those disclosed in WO2000/017165, WO2005/095409, WO2005/097806, WO 2007/128568, WO2008/009435, WO 2009/059943 and WO2009/071509.

The term "NEP inhibitor" refers to a compound that inhibits neutral endopeptidase (NEP) EC 3.4.24.11. Examples include Candoxatril, Candoxatrilat, Dexecadotril, Ecadotril, Racecadotril, Sampatrilat, Fasidotril, Omapatrilat, Gemopatrilat, Daglutril, SCH-42495, SCH-32615, UK-447841, AVE-0848, PL-37 and (2R,4S)-5-Biphenyl-4-yl-4-(3-carboxy-propionylamino)-2-methyl-pentanoic acid ethyl ester or a pharmaceutically acceptable salt thereof. NEP inhibitors also include Phosphono/biaryl substituted dipeptide derivatives, as disclosed in U.S. Pat. No. 5,155, 100. NEP inhibitors also include N-mercaptoacyl phenylalanine derivative as disclosed in PCT application Number WO 2003/104200. NEP inhibitors also include dual-acting antihypertensive agents as disclosed in PCT application Numbers WO 2008/133896, WO 2009/035543 or WO 2009/134741. Other examples include compounds disclosed in U.S. application Ser. Nos. 12/788,794; 12/788,766 and 12/947,029. NEP inhibitors also include compounds disclosed in WO 2010/136474, WO 2010/136493, WO 2011/061271 and U.S. provisional applications Nos. 61/414,171 and 61/414,163.

The invention is further illustrated by the following example, which is not intended to limit the scope of the claims.

EXAMPLE

We targeted PTPσ using both genetic and pharmacologic approaches in order to promote reinnervation of a myocardial infarct, and used electrocardiogram (ECG) telemetry to examine arrhythmia susceptibility. Restoring sympathetic innervation to the infarct and the surrounding tissue decreased arrhythmia susceptibility and normalized cardiac electrophysiology and $Ca^{2+}$ dynamics, despite the presence of a scar.

Methods

PTPσ (ptprs) transgenic mice (BalbC) were supplied by Michel Tremblay (McGill University), and were bred as heterozygotes. Age and gender-matched mice 12-18 weeks old were used for all experiments. All procedures were approved by Institutional Animal Care and Use Committees and comply with the Guide for the Care and Use of Laboratory Animals published by the National Academies Press (8th edition).

Myocardial ischemia-reperfusion (I-R) was carried out as described. Anesthesia was induced with 4% isoflurane and maintained with 2% isoflurane. The left anterior descending coronary artery (LAD) was reversibly ligated for 30 min (telemetry studies) or 45 min (ex vivo mapping) and then reperfused by release of the ligature.

In vivo telemetry devices were implanted 5 days prior to I-R surgery 16. Arrhythmias were induced by IP injection of 10 g isoproterenol (ISO) 10 days after I-R. Some mice were given daily IP injections of vehicle (5% DMSO/Saline), IMP (Intracellular Mu Peptide; 10 μmol), or ISP (Intracellular Sigma Peptide, 10 μmol) beginning 3 days after I-R.

Immunohistochemistry for tyrosine hydroxylase (TH; sympathetic nerve fibers) and fibrinogen (Fib; infarct/scar) was carried out as described previously. Sympathetic nerve density and infarct size were quantified using ImageJ.

Norepinephrine (NE) content was quantified by HPLC.

Statistics

Data were analyzed by t-test, one-way ANOVA, or two-way ANOVA depending on the number and size of groups. Analyses were carried out using Prism 5.0.

Results

Targeting PTPσ Restores Sympathetic Innervation after MI and Prevents Ventricular Arrhythmias We found that CSPGs generated in the cardiac scar after ischemia reperfusion prevented reinnervation of the infarct (FIG. 1A) despite high levels of NGF (Nerve Growth Factor) in the scar. We also found the infarct becomes hyperinnervated in animals lacking the CSPG receptor PTPσ (FIG. 1B), confirming the crucial role for PTPσ in sympathetic denervation after MI. Since cardiac denervation is linked to risk for arrhythmia and cardiac arrest in human studies, we investigated restoring sympathetic innervation to the infarct and surrounding myocardium affected arrhythmia susceptibility. Control mice (ptprs+/−; HET) and mice lacking PTPσ (ptprs−/−; KO) were implanted with ECG telemetry transmitters and then subjected to sham or MI surgery.

Ten days after surgery, mice were injected with 10 µg of the beta agonist isoproterenol (ISO) to mimic circulating catecholamines and provoke arrhythmias. ISO stimulated comparable increases in heart rate in all mice (FIG. 1C), but the arrhythmia response differed based on the innervation status of the infarct. Isoproterenol stimulated few premature ventricular complexes (PVCs) in sham mice of either genotype, but triggered a significant number of PVCs in HET mice with denervated infarcts (FIG. 1E). In contrast, KO mice with innervated infarcts were resistant to ISO-induced arrhythmias, having the same number of PVCs as sham animals (FIG. 1E). The infarct size in both genotypes was the same (FIG. 1D), indicating the difference in arrhythmia susceptibility could not be explained by scar size.

To confirm that reinnervation of the infarct and surrounding tissue decreased arrhythmia susceptibility, we sought to restore innervation in mice expressing normal levels of PTPσ. In order to promote regeneration of sympathetic axons through the CSPG-rich cardiac scar, we utilized Intracellular Sigma Peptide (ISP) (SEQ ID NO: 57) to target the intracellular dimerization domain of PTPσ. ISP restored growth of CNS axons through CSPGs in vitro, and systemic injections of ISP enhanced axon sprouting through CSPGs after spinal cord injury in vivo. We investigated if targeting PTPσ with ISP could restore sympathetic axon regeneration into the cardiac scar. Wildtype (ptprs+/+) mice were implanted with ECG telemetry transmitters, and a week later subjected to ischemia-reperfusion surgery. Beginning three days after MI, when the infarct was fully denervated, mice were injected daily (IP) with vehicle (5% DMSO/Saline), ISP (10 µmol; 44 µg) or IMP (Intracellular Mu Peptide) as a negative control (10 µmol; 42 µg). IMP targets the receptor PTPµ, which is not present in sympathetic neurons. Fourteen days after the MI surgery, mice were treated with ISO to mimic circulating catecholamines and provoke arrhythmias, and hearts were collected for analysis of sympathetic innervation. Animals treated with either vehicle or IMP had denervated infarcts (FIG. 2 A, B), whereas animals treated with ISP had normal levels of sympathetic innervation throughout the left ventricle, including the infarct (FIG. 2C). Thus, daily ISP injections beginning 3 days after the injury, when denervation was well established, allowed robust regeneration of sympathetic axons into the CSPG-laden cardiac scar.

Several studies indicate that newly regenerating sympathetic axons in the damaged heart have low levels of NE, likely due to local depletion of TH by inflammatory cytokines. The cardiac scar in mouse heart is mature by 10-12 days after reperfusion and acute inflammation has resolved. Therefore, we quantified NE levels in the infarct and peri-infarct myocardium 14 days after surgery to determine if the axons that had reinnervated the infarct and surrounding myocardium had normal NE levels. NE content was low in the denervated infarct of vehicle-treated animals, but was normal in the innervated infarct of ISP-treated animals (FIG. 2E). NE content in the undamaged portion of the left ventricle was similar in both treatment groups (FIG. 2E), consistent with identical innervation densities (FIG. 2D). Likewise, NE content in the undamaged right ventricle was similar in both groups (data not shown). These data indicate that restoring innervation to the infarct with ISP normalizes NE levels across the left ventricle by two weeks after MI.

Since regional sympathetic denervation is thought to be an important source of post-MI arrhythmia susceptibility, we quantified ISO-induced arrhythmias 14 days after MI in mice treated with vehicle, IMP, or ISP. Isoproterenol triggered significantly fewer PVCs in ISP-treated mice, which had innervated infarcts and normal NE content, than in the vehicle or IMP treated groups which had denervated infarcts and low NE content (FIG. 2F). These data suggest that restoring sympathetic transmission throughout the infarcted left ventricle, even days after denervation is established, is sufficient to decrease arrhythmia susceptibility.

We found that targeting PTPσ can promote nerve regeneration through CSPG-containing scars in vivo, and confirm the efficacy of the therapeutic peptide ISP. Our data indicate that the peptide ISP is effective in disrupting PTPσ in vivo and is able to restore axon regeneration through CSPGs when appropriate growth factors are present. It is especially notable that we were able to restore innervation using a pharmacologic intervention begun several days after injury when the infarct and peri-infarct myocardium was denervated. Daily injections with ISP were sufficient to restore functional sympathetic innervation, and reinnervation rendered hearts surprisingly resistant to arrhythmias. Indeed, infarcted hearts with restored sympathetic innervation were electrically indistinguishable from sham hearts, despite the presence of a scar. These data show that targeting PTPσ using a simple systemically deliverable peptide in patients who have survived a myocardial infarction can promote reinnervation of otherwise denervated cardiac tissue, and that normalizing the innervation can decrease arrhythmia risk.

From the above description of the invention, those skilled in the art will perceive improvements, changes and modifications. Such improvements, changes, and modifications are within the skill of the art and are intended to be covered by the appended claims. All patents and publications identified herein are incorporated by reference in their entirety.

Having described the invention, we claim:

1. A method of treating heart disease or injury a subject in need thereof, the method comprising:
administering to the subject a therapeutic agent that inhibits one or more of catalytic activity, signaling, and function of PTPσ, wherein the therapeutic agent comprises a therapeutic peptide with a sequence selected from the group consisting of SEQ ID NOs: 1-25 and 32.

2. The method of claim 1, wherein the therapeutic peptide consists of the sequence set forth in SEQ ID NO: 32.

3. The method of claim 1, wherein the therapeutic agent includes a transport moiety that is linked to the therapeutic peptide and facilitates uptake of the therapeutic peptides by a cell of the heart being treated.

4. The method of claim 3, wherein the transport moiety is an HIV Tat transport moiety.

5. The method of claim 3, wherein the therapeutic agent is administered systemically to the subject being treated.

6. The method of claim 1, wherein the heart disease or injury comprises at least one of myocardial infarction, myocardial ischemia/reperfusion injury, cardiac denervation hypersensitivity, or arrhythmia.

7. The method of claim 6, wherein the heart injury is a myocardial infarction and the therapeutic agent is administered to the infarct or peri-infarct region of the heart.

8. A method of treating arrhythmia in a subject in need thereof, the method comprising:
    administering to cardiac tissue of the subject a therapeutically effective amount of a therapeutic agent that inhibits one or more of catalytic activity, signaling, and/or function of PTPσ, wherein the therapeutic agent comprises a therapeutic peptide with a sequence selected from the group consisting of SEQ ID NOs: 1-25 and 32.

9. The method of claim 8, wherein the therapeutic peptide consists of the sequence set forth in SEQ ID NO: 32.

10. The method of claim 8, wherein the therapeutic agent includes a transport moiety that is linked to the therapeutic peptide and facilitates uptake of the therapeutic peptides by a cell of the heart being treated.

11. The method of claim 10, wherein the transport moiety is an HIV Tat transport moiety.

12. The method of claim 10, wherein the therapeutic agent is administered systemically to the subject being treated.

13. A method of treating heart disease or injury in a subject in need thereof, the method comprising:
    administering to the subject a therapeutic agent that inhibits one or more of catalytic activity, signaling, and function of PTPσ, wherein the therapeutic agent comprises a therapeutic peptide that has at least about 85% sequence identity to the amino acid sequence of SEQ ID NO: 32.

14. The method of claim 13, wherein the therapeutic peptide includes a conservative substitution of an amino acid of at least one of residue 4,5, 6,7,9,10,12, or 13 of SEQ ID NO: 32.

15. A method of treating arrhythmia in a subject in need thereof, the method comprising:
    administering to cardiac tissue of the subject a therapeutically effective amount of a therapeutic agent that inhibits one or more of catalytic activity, signaling, and/or function of PTPσ, wherein the therapeutic agent comprises a therapeutic peptide that has at least about 85% sequence identity to the amino acid sequence of SEQ ID NO: 32.

16. The method of claim 15, wherein the therapeutic peptide includes a conservative substitution of an amino acid of at least one of residue 4,5, 6,7,9,10,12, or 13 of SEQ ID NO: 32.

* * * * *

SEQUENCE LISTING

<160> NUMBER OF SEQ ID NOS: 58

<210> SEQ ID NO 1
<211> LENGTH: 22
<212> TYPE: PRT
<213> ORGANISM: Xenopus borealis

<400> SEQUENCE: 1

Asp Leu Ala Glu His Thr Glu His Leu Lys Ala Asn Asp Asn Leu Lys
1               5                   10                  15

Ser Gln Glu Tyr Glu Ser
            20

```
<210> SEQ ID NO 2
<211> LENGTH: 21
<212> TYPE: PRT
<213> ORGANISM: Anolis carolinensis

<400> SEQUENCE: 2

Asp His Thr Glu His Leu Lys Ala Asn Asp Asn Leu Lys Leu Ser Gln
1               5                   10                  15

Glu Tyr Glu Ser Ile
            20

<210> SEQ ID NO 3
<211> LENGTH: 24
<212> TYPE: PRT
<213> ORGANISM: Danio rerio

<400> SEQUENCE: 3

Glu Leu Ala Glu His Thr Glu Leu Leu Lys Ala Asn Asp Asn Leu Lys
1               5                   10                  15

Leu Ser Gln Glu Tyr Glu Ser Ile
            20

<210> SEQ ID NO 4
<211> LENGTH: 24
<212> TYPE: PRT
<213> ORGANISM: Oreochromis aureus

<400> SEQUENCE: 4

Glu Leu Ala Glu His Thr Glu Leu Leu Lys Ala Asn Asp Asn Leu Lys
1               5                   10                  15

Leu Ser Gln Glu Tyr Glu Ser Ile
            20

<210> SEQ ID NO 5
<211> LENGTH: 24
<212> TYPE: PRT
<213> ORGANISM: Gallus gallus

<400> SEQUENCE: 5

Glu Leu Ala Glu His Thr Glu His Leu Lys Ala Asn Asp Asn Leu Lys
1               5                   10                  15

Leu Ser Gln Glu Tyr Glu Ser Ile
            20

<210> SEQ ID NO 6
<211> LENGTH: 24
<212> TYPE: PRT
<213> ORGANISM: Fringilla coelebs

<400> SEQUENCE: 6

Glu Leu Ala Glu His Thr Glu His Leu Lys Ala Asn Asp Asn Leu Lys
1               5                   10                  15

Leu Ser Gln Glu Tyr Glu Ser Ile
            20

<210> SEQ ID NO 7
<211> LENGTH: 24
<212> TYPE: PRT
<213> ORGANISM: Ornithorhynchus anatinus
```

-continued

<400> SEQUENCE: 7

Glu Leu Ala Glu His Thr Asp His Leu Lys Ala Asn Asp Asn Leu Lys
1               5                   10                  15

Leu Ser Gln Glu Tyr Glu Ser Ile
            20

<210> SEQ ID NO 8
<211> LENGTH: 24
<212> TYPE: PRT
<213> ORGANISM: Sarcophilus harrisii

<400> SEQUENCE: 8

Glu Met Ala Glu His Thr Glu His Leu Lys Ala Asn Asp Asn Leu Lys
1               5                   10                  15

Leu Ser Gln Glu Tyr Glu Ser Ile
            20

<210> SEQ ID NO 9
<211> LENGTH: 24
<212> TYPE: PRT
<213> ORGANISM: Mustela putorius

<400> SEQUENCE: 9

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 10
<211> LENGTH: 24
<212> TYPE: PRT
<213> ORGANISM: Galago alleni

<400> SEQUENCE: 10

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 11
<211> LENGTH: 24
<212> TYPE: PRT
<213> ORGANISM: Callithrix aurita

<400> SEQUENCE: 11

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 12
<211> LENGTH: 24
<212> TYPE: PRT
<213> ORGANISM: Rattus rattus

<400> SEQUENCE: 12

Asp Met Ala Glu His Met Glu Arg Leu Lys Ala Asn Asp Ser Leu Lys
1               5                   10                  15

Leu Ser Gln Glu Tyr Glu Ser Ile
            20

```
<210> SEQ ID NO 13
<211> LENGTH: 24
<212> TYPE: PRT
<213> ORGANISM: Mus musculus

<400> SEQUENCE: 13

Asp Met Ala Glu His Met Glu Arg Leu Lys Ala Asn Asp Ser Leu Lys
1               5                   10                  15

Leu Ser Gln Glu Tyr Glu Ser Ile
            20

<210> SEQ ID NO 14
<211> LENGTH: 24
<212> TYPE: PRT
<213> ORGANISM: Canis familiaris

<400> SEQUENCE: 14

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 15
<211> LENGTH: 24
<212> TYPE: PRT
<213> ORGANISM: Sus barbatus

<400> SEQUENCE: 15

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 16
<211> LENGTH: 24
<212> TYPE: PRT
<213> ORGANISM: Bos taurus

<400> SEQUENCE: 16

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 17
<211> LENGTH: 24
<212> TYPE: PRT
<213> ORGANISM: Ovis aries

<400> SEQUENCE: 17

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 18
<211> LENGTH: 24
<212> TYPE: PRT
<213> ORGANISM: Orcinus orca
```

-continued

<400> SEQUENCE: 18

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 19
<211> LENGTH: 24
<212> TYPE: PRT
<213> ORGANISM: Saimiri sciureus

<400> SEQUENCE: 19

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 20
<211> LENGTH: 24
<212> TYPE: PRT
<213> ORGANISM: Papio hamadryas

<400> SEQUENCE: 20

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 21
<211> LENGTH: 24
<212> TYPE: PRT
<213> ORGANISM: Primate calicivirus

<400> SEQUENCE: 21

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 22
<211> LENGTH: 24
<212> TYPE: PRT
<213> ORGANISM: Primate calicivirus

<400> SEQUENCE: 22

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 23
<211> LENGTH: 24
<212> TYPE: PRT
<213> ORGANISM: Macaca radiata

<400> SEQUENCE: 23

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 24
<211> LENGTH: 24
<212> TYPE: PRT
<213> ORGANISM: Pan troglodytes

<400> SEQUENCE: 24

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 25
<211> LENGTH: 24
<212> TYPE: PRT
<213> ORGANISM: Homo sapiens

<400> SEQUENCE: 25

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 26
<211> LENGTH: 24
<212> TYPE: PRT
<213> ORGANISM: Homo sapiens

<400> SEQUENCE: 26

Asp Leu Ala Asp Asn Ile Glu Arg Leu Lys Ala Asn Asp Gly Leu Lys
1               5                   10                  15

Phe Ser Gln Glu Tyr Glu Ser Ile
            20

<210> SEQ ID NO 27
<211> LENGTH: 24
<212> TYPE: PRT
<213> ORGANISM: Homo sapiens

<400> SEQUENCE: 27

Glu Leu Ala Asp His Ile Glu Arg Leu Lys Ala Asn Asp Asn Leu Lys
1               5                   10                  15

Phe Ser Gln Glu Tyr Glu Ser Ile
            20

<210> SEQ ID NO 28
<211> LENGTH: 24
<212> TYPE: PRT
<213> ORGANISM: Homo sapiens

<400> SEQUENCE: 28

Lys Leu Glu Glu Glu Ile Asn Arg Arg Met Ala Asp Asp Asn Lys Ile
1               5                   10                  15

Phe Arg Glu Glu Phe Asn Ala Leu
            20

<210> SEQ ID NO 29
<211> LENGTH: 10
<212> TYPE: PRT
<213> ORGANISM: Homo sapiens

<400> SEQUENCE: 29

Asp Met Ala Glu His Thr Glu Arg Leu Lys
1               5                   10

```
<210> SEQ ID NO 30
<211> LENGTH: 4
<212> TYPE: PRT
<213> ORGANISM: Homo sapiens

<400> SEQUENCE: 30

Ala Asn Asp Ser
1

<210> SEQ ID NO 31
<211> LENGTH: 10
<212> TYPE: PRT
<213> ORGANISM: Homo sapiens

<400> SEQUENCE: 31

Leu Lys Leu Ser Gln Glu Tyr Glu Ser Ile
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is Thr or Met

<400> SEQUENCE: 32

Glu His Xaa Glu Arg Leu Lys Ala Asn Asp Ser Leu Lys Leu
1               5                   10

<210> SEQ ID NO 33
<211> LENGTH: 33
<212> TYPE: PRT
<213> ORGANISM: Artificial Sequence
<220> FEATURE:
<223> OTHER INFORMATION: Synthetic Construct

<400> SEQUENCE: 33

Gly Arg Lys Lys Arg Arg Gln Arg Arg Arg Cys Asp Leu Ala Glu His
1               5                   10                  15

Thr Glu His Leu Lys Ala Asn Asp Asn Leu Lys Ser Gln Glu Tyr Glu
                20                  25                  30

Ser

<210> SEQ ID NO 34
<211> LENGTH: 32
<212> TYPE: PRT
<213> ORGANISM: Artificial Sequence
<220> FEATURE:
<223> OTHER INFORMATION: Synthetic Construct

<400> SEQUENCE: 34

Gly Arg Lys Lys Arg Arg Gln Arg Arg Arg Cys Asp His Thr Glu His
1               5                   10                  15

Leu Lys Ala Asn Asp Asn Leu Lys Leu Ser Gln Glu Tyr Glu Ser Ile
                20                  25                  30

<210> SEQ ID NO 35
<211> LENGTH: 35
<212> TYPE: PRT
<213> ORGANISM: Artificial Sequence
<220> FEATURE:
<223> OTHER INFORMATION: Synthetic Construct
```

```
<400> SEQUENCE: 35

Gly Arg Lys Lys Arg Arg Gln Arg Arg Cys Glu Leu Ala Glu His
1               5                   10                  15

Thr Glu Leu Leu Lys Ala Asn Asp Asn Leu Lys Leu Ser Gln Glu Tyr
            20                  25                  30

Glu Ser Ile
        35

<210> SEQ ID NO 36
<211> LENGTH: 35
<212> TYPE: PRT
<213> ORGANISM: Artificial Sequence
<220> FEATURE:
<223> OTHER INFORMATION: Synthetic Construct

<400> SEQUENCE: 36

Gly Arg Lys Lys Arg Arg Gln Arg Arg Cys Glu Leu Ala Glu His
1               5                   10                  15

Thr Glu Leu Leu Lys Ala Asn Asp Asn Leu Lys Leu Ser Gln Glu Tyr
            20                  25                  30

Glu Ser Ile
        35

<210> SEQ ID NO 37
<211> LENGTH: 35
<212> TYPE: PRT
<213> ORGANISM: Artificial Sequence
<220> FEATURE:
<223> OTHER INFORMATION: Synthetic Construct

<400> SEQUENCE: 37

Gly Arg Lys Lys Arg Arg Gln Arg Arg Cys Glu Leu Ala Glu His
1               5                   10                  15

Thr Glu His Leu Lys Ala Asn Asp Asn Leu Lys Leu Ser Gln Glu Tyr
            20                  25                  30

Glu Ser Ile
        35

<210> SEQ ID NO 38
<211> LENGTH: 35
<212> TYPE: PRT
<213> ORGANISM: Artificial Sequence
<220> FEATURE:
<223> OTHER INFORMATION: Synthetic Construct

<400> SEQUENCE: 38

Gly Arg Lys Lys Arg Arg Gln Arg Arg Cys Glu Leu Ala Glu His
1               5                   10                  15

Thr Glu His Leu Lys Ala Asn Asp Asn Leu Lys Leu Ser Gln Glu Tyr
            20                  25                  30

Glu Ser Ile
        35

<210> SEQ ID NO 39
<211> LENGTH: 35
<212> TYPE: PRT
<213> ORGANISM: Artificial Sequence
<220> FEATURE:
<223> OTHER INFORMATION: Synthetic Construct
```

```
<400> SEQUENCE: 39

Gly Arg Lys Lys Arg Arg Gln Arg Arg Cys Glu Leu Ala Glu His
1               5                   10                  15

Thr Asp His Leu Lys Ala Asn Asp Asn Leu Lys Leu Ser Gln Glu Tyr
            20                  25                  30

Glu Ser Ile
        35

<210> SEQ ID NO 40
<211> LENGTH: 35
<212> TYPE: PRT
<213> ORGANISM: Artificial Sequence
<220> FEATURE:
<223> OTHER INFORMATION: Synthetic Construct

<400> SEQUENCE: 40

Gly Arg Lys Lys Arg Arg Gln Arg Arg Cys Glu Met Ala Glu His
1               5                   10                  15

Thr Glu His Leu Lys Ala Asn Asp Asn Leu Lys Leu Ser Gln Glu Tyr
            20                  25                  30

Glu Ser Ile
        35

<210> SEQ ID NO 41
<211> LENGTH: 35
<212> TYPE: PRT
<213> ORGANISM: Artificial Sequence
<220> FEATURE:
<223> OTHER INFORMATION: Synthetic Construct

<400> SEQUENCE: 41

Gly Arg Lys Lys Arg Arg Gln Arg Arg Cys Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 42
<211> LENGTH: 35
<212> TYPE: PRT
<213> ORGANISM: Artificial Sequence
<220> FEATURE:
<223> OTHER INFORMATION: Synthetic Construct

<400> SEQUENCE: 42

Asp Met Ala Glu His Thr Glu Arg Leu Lys Ala Asn Asp Ser Leu Lys
1               5                   10                  15

Leu Ser Gln Glu Tyr Glu Ser Ile Gly Arg Lys Lys Arg Arg Gln Arg
            20                  25                  30

Arg Arg Cys
        35

<210> SEQ ID NO 43
<211> LENGTH: 35
<212> TYPE: PRT
<213> ORGANISM: Artificial Sequence
<220> FEATURE:
<223> OTHER INFORMATION: Synthetic Peptide
```

```
<400> SEQUENCE: 43

Gly Arg Lys Lys Arg Arg Gln Arg Arg Cys Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 44
<211> LENGTH: 35
<212> TYPE: PRT
<213> ORGANISM: Artificial Sequence
<220> FEATURE:
<223> OTHER INFORMATION: Synthetic Construct

<400> SEQUENCE: 44

Gly Arg Lys Lys Arg Arg Gln Arg Arg Cys Asp Met Ala Glu His
1               5                   10                  15

Met Glu Arg Leu Lys Ala Asn Asp Ser Leu Lys Leu Ser Gln Glu Tyr
            20                  25                  30

Glu Ser Ile
        35

<210> SEQ ID NO 45
<211> LENGTH: 35
<212> TYPE: PRT
<213> ORGANISM: Artificial Sequence
<220> FEATURE:
<223> OTHER INFORMATION: Synthetic Construct

<400> SEQUENCE: 45

Gly Arg Lys Lys Arg Arg Gln Arg Arg Cys Asp Met Ala Glu His
1               5                   10                  15

Met Glu Arg Leu Lys Ala Asn Asp Ser Leu Lys Leu Ser Gln Glu Tyr
            20                  25                  30

Glu Ser Ile
        35

<210> SEQ ID NO 46
<211> LENGTH: 35
<212> TYPE: PRT
<213> ORGANISM: Artificial Sequence
<220> FEATURE:
<223> OTHER INFORMATION: Synthetic Construct

<400> SEQUENCE: 46

Gly Arg Lys Lys Arg Arg Gln Arg Arg Cys Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 47
<211> LENGTH: 35
<212> TYPE: PRT
<213> ORGANISM: Artificial Sequence
<220> FEATURE:
<223> OTHER INFORMATION: Synthetic Construct
```

```
<400> SEQUENCE: 47

Gly Arg Lys Lys Arg Arg Gln Arg Arg Arg Cys Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 48
<211> LENGTH: 35
<212> TYPE: PRT
<213> ORGANISM: Artificial Sequence
<220> FEATURE:
<223> OTHER INFORMATION: Synthetic Construct

<400> SEQUENCE: 48

Gly Arg Lys Lys Arg Arg Gln Arg Arg Arg Cys Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 49
<211> LENGTH: 35
<212> TYPE: PRT
<213> ORGANISM: Artificial Sequence
<220> FEATURE:
<223> OTHER INFORMATION: Synthetic Construct

<400> SEQUENCE: 49

Gly Arg Lys Lys Arg Arg Gln Arg Arg Arg Cys Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 50
<211> LENGTH: 35
<212> TYPE: PRT
<213> ORGANISM: Artificial Sequence
<220> FEATURE:
<223> OTHER INFORMATION: Synthetic Construct

<400> SEQUENCE: 50

Gly Arg Lys Lys Arg Arg Gln Arg Arg Arg Cys Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 51
<211> LENGTH: 35
<212> TYPE: PRT
<213> ORGANISM: Artificial Sequence
<220> FEATURE:
<223> OTHER INFORMATION: Synthetic Construct
```

<400> SEQUENCE: 51

Gly Arg Lys Lys Arg Arg Gln Arg Arg Arg Cys Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 52
<211> LENGTH: 35
<212> TYPE: PRT
<213> ORGANISM: Artificial Sequence
<220> FEATURE:
<223> OTHER INFORMATION: Synthetic Construct

<400> SEQUENCE: 52

Gly Arg Lys Lys Arg Arg Gln Arg Arg Arg Cys Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 53
<211> LENGTH: 35
<212> TYPE: PRT
<213> ORGANISM: Artificial Sequence
<220> FEATURE:
<223> OTHER INFORMATION: Synthetic Construct

<400> SEQUENCE: 53

Gly Arg Lys Lys Arg Arg Gln Arg Arg Arg Cys Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 54
<211> LENGTH: 35
<212> TYPE: PRT
<213> ORGANISM: Artificial Sequence
<220> FEATURE:
<223> OTHER INFORMATION: Synthetic Construct

<400> SEQUENCE: 54

Gly Arg Lys Lys Arg Arg Gln Arg Arg Arg Cys Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 55
<211> LENGTH: 35
<212> TYPE: PRT
<213> ORGANISM: Artificial Sequence
<220> FEATURE:
<223> OTHER INFORMATION: Synthetic Construct

```
<400> SEQUENCE: 55

Gly Arg Lys Lys Arg Arg Gln Arg Arg Cys Asp Met Ala Glu His
1               5                   10                  15

Thr Glu Arg Leu Lys Ala Asn Asp Ser Leu Lys Leu Ser Gln Glu Tyr
                20                  25                  30

Glu Ser Ile
        35

<210> SEQ ID NO 56
<211> LENGTH: 35
<212> TYPE: PRT
<213> ORGANISM: Artificial Sequence
<220> FEATURE:
<223> OTHER INFORMATION: Synthetic Construct

<400> SEQUENCE: 56

Gly Arg Lys Lys Arg Arg Gln Arg Arg Cys Asp Met Ala Glu His
1               5                   10                  15

Thr Glu Arg Leu Lys Ala Asn Asp Ser Leu Lys Leu Ser Gln Glu Tyr
                20                  25                  30

Glu Ser Ile
        35

<210> SEQ ID NO 57
<211> LENGTH: 35
<212> TYPE: PRT
<213> ORGANISM: Artificial Sequence
<220> FEATURE:
<223> OTHER INFORMATION: Synthetic Construct

<400> SEQUENCE: 57

Gly Arg Lys Lys Arg Arg Gln Arg Arg Cys Glu Leu Ala Asp His
1               5                   10                  15

Ile Glu Arg Leu Lys Ala Asn Asp Asn Leu Lys Phe Ser Gln Glu Tyr
                20                  25                  30

Glu Ser Ile
        35

<210> SEQ ID NO 58
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (14)..(14)
<223> OTHER INFORMATION: Xaa is Thr or Met

<400> SEQUENCE: 58

Gly Arg Lys Lys Arg Arg Gln Arg Arg Cys Glu His Xaa Glu Arg
1               5                   10                  15

Leu Lys Ala Asn Asp Ser Leu Lys Leu
                20                  25
```